US008236973B2

(12) United States Patent
Liu et al.

(10) Patent No.: US 8,236,973 B2
(45) Date of Patent: Aug. 7, 2012

(54) ADSORPTION SEPARATION PROCESSES FOR IONIC LIQUID CATALYTIC PROCESSES

(75) Inventors: Wei Liu, Richland, WA (US); John E. Holladay, Kennewick, WA (US); Feng Zheng, Richland, WA (US); Heather M. Brown, Kennewick, WA (US); Alan R. Cooper, Richland, WA (US)

(73) Assignee: Battelle Memorial Institute, Richland, WA (US)

( * ) Notice: Subject to any disclaimer, the term of this patent is extended or adjusted under 35 U.S.C. 154(b) by 370 days.

(21) Appl. No.: 12/756,916

(22) Filed: Apr. 8, 2010

(65) Prior Publication Data

US 2011/0105770 A1    May 5, 2011

Related U.S. Application Data

(60) Provisional application No. 61/258,347, filed on Nov. 5, 2009.

(51) Int. Cl.
*C07D 307/42* (2006.01)
*C07D 307/45* (2006.01)
*C07D 493/04* (2006.01)

(52) U.S. Cl. ........................................ 549/488; 549/464

(58) Field of Classification Search .................. 549/464, 549/488

See application file for complete search history.

(56) References Cited

U.S. PATENT DOCUMENTS

| | | | |
|---|---|---|---|
| 6,518,440 | B2 | 2/2003 | Lightner |
| 2008/0033187 | A1 | 2/2008 | Zhao et al. |
| 2009/0018352 | A1 | 1/2009 | Geier et al. |
| 2009/0030215 | A1 | 1/2009 | Dignan et al. |
| 2009/0270608 | A1 | 10/2009 | Zhang et al. |

FOREIGN PATENT DOCUMENTS

| | | |
|---|---|---|
| EP | 2033958 | 11/2009 |
| EP | 2034005 | 11/2009 |
| WO | WO 2006/063220 | 6/2006 |
| WO | WO 2008/019219 | 2/2008 |
| WO | WO2008/157617 | 12/2008 |
| WO | WO2009/012445 | 1/2009 |
| WO | WO2009/030504 | 3/2009 |
| WO | WO2009/030505 | 3/2009 |
| WO | WO2009/030506 | 3/2009 |
| WO | WO2009/030507 | 3/2009 |
| WO | WO2009/030508 | 3/2009 |
| WO | WO2009/030509 | 3/2009 |
| WO | WO2009/030510 | 3/2009 |
| WO | WO2009/030511 | 3/2009 |
| WO | WO2009/030512 | 3/2009 |

OTHER PUBLICATIONS

Huang, H.G. et al., "A review of separation technologies in current and future biorefineries," *Separation and Purification Technology*, vol. 62, pp. 1-21 (2008).

International Search Report and Written Opinion for PCT/US2010/047459, filed Sep. 1, 2010 (mailed May 30, 2011).
Azevedo, D. et al., "Fructose-Glucose Separation in a SMB Pilot Unit: Modeling, Simulation, Design, and Operation," *AIChE Journal*, vol. 47, No. 9, pp. 2042-2051 (Sep. 2001).
Bonn, G., "High-Performance Liquid Chromatographic Elution Behaviour of Oligosaccharides, Monosaccharides and Sugar Degradation Products on Series-Connected Ion-Exchange Resin Columns Using Water as the Mobile Phase," *Journal of Chromatography*, vol. 322, pp. 411-424 (1985).
Dieter, K. et al., "Ionic Structure and Interactions in 1-Methyl-3-ethylimidazolium Chloride-AICI$_3$ Molten Salts," *J. Am. Chem. Soc.*, vol. 110, pp. 2722-2726 (1988).
Hattori, H. et al., "Selective Adsorption of a Substance Derived from Saccharides onto Synthetic Resin Particles," *Adsorption*, vol. 11, pp. 917-920 (2005).
Holbrey, J.D. et al., "Ionic Liquids," *Clean Products and Processes*, vol. 1, pp. 223-236 (1999).
Lansalot-Matras, C. et al., "Dehydration of fructose into 5-hydroxymethylfurfural in the presence of ionic liquids," *Catalysis Communications*, vol. 4, pp. 517-520 (2003).
Moreau, C. et al., "Dehydration of fructose and sucrose into 5-hydroxymethylfurfural in the presence of 1-H-3-methyl imidazolium chloride acting both as solvent and catalyst," *Journal of Molecular Catalysis A: Chemical*, vol. 253, pp. 165-169 (2006).
Vinke, P. et al., "The Dehydration of Fructose Towards 5-Hydroxymethylfurfural Using Activated Carbon as Adsorbent," *Starch/Stärke*, vol. 44, No. 3, pp. 90-96 (1992).
Wankat, P., "Large-Scale Chromatography," in *Handbook of Separation Process Technology*, Ch. 14, pp. 733-759 (1987).
Xie, Y. et al., "Comparison of Two Adsorbents for Sugar Recovery from Biomass Hydrolyzate," *Ind. Eng. Chem. Res.*, vol. 44, No. 17, pp. 6816-6823 (2005).
Zhao, H. et al., "Metal Chlorides in Ionic Liquid Solvents Convert Sugars to 5-Hydroxymethylfurfural," *Science*, vol. 316, pp. 1597-1600 (Jun. 15, 2007).
Arora, M.B. et al., "The separative bioreactor: A continuous separation process for the simultaneous production and direct capture of organic acids," *Separation Science and Technology*, vol. 42, No. 11, pp. 2519-2538 (2007).
Azevedo, DCS et al., "Fructose-glucose separation in a SMB pilot unit: Modeling, simulation, design, and operation," *AIChE Journal*, vol. 47, No. 9, pp. 2042-2051 (Sep. 2001).
Azevedo, DCS et al., "Separation of fructose and glucose from cashew apple juice by SMB chromatography," *Separation Science and Technology*, vol. 40, No. 9, pp. 1761-1780 (2005).
Casillas, J.L. et al., "The Use of Modified Divinylbenzene Polystyrene Resins in the Separation of Fermentation Products—A Case-Study Utilizing Amino-Acids and a Dipeptide," *Journal of Chemical Technology and Biotechnology*, vol. 55, No. 2, pp. 163-169 (1992).

(Continued)

*Primary Examiner* — Bernard Dentz
(74) *Attorney, Agent, or Firm* — Klarquist Sparkman, LLP

(57) ABSTRACT

Presently disclosed are methods and apparatus for separation of reaction products from reaction mixtures in an ionic liquid catalysis process, particularly in conversion of biomass, cellulose, and sugars into chemical intermediates such as 5-hydroxymethylfurfural (HMF). In one embodiment an ion exclusion adsorption mechanism is used for the separation process. The process comprises (i) mixing the ionic liquid-containing reaction mixture with de-ionized water, (ii) flowing the water solution mixture into an adsorption column, (iii) eluting the column with a water- and/or alcohol-based fluid, and (iv) collecting separated fractions at different elution times.

26 Claims, 15 Drawing Sheets

OTHER PUBLICATIONS

Ching, C.B. et al., "Experimental-Study of a Simulated Countercurrent Adsorption System .5. Comparison of Resin and Zeolite Absorbents for Fructose Glucose Separation at High-Concentration," *Chemical Engineering Science*, vol. 42, No. 11, pp. 2547-2555 (1987).

da Silva, EAB et al., "Analysis of the high-fructose syrup production using reactive SMB technology," *Chemical Engineering Journal*, vol. 118, No. 3, pp. 167-181 (May 15, 2006).

Gramblicka, M. et al., "Adsorption equilibria of glucose, fructose, sucrose, and fructooligosaccharides on cation exchange resins," *Journal of Chemical and Engineering Data*, vol. 52, No. 2, pp. 345-350 (Mar.-Apr. 2007).

Heper, M. et al., "Sodium, ammonium, calcium, and magnesium forms of zeolite Y for the adsorption of glucose and fructose from aqueous solutions," *Journal of Colloid and Interface Science*, vol. 306, No. 1, pp. 11-15 (Feb. 1, 2007).

Ho, C. et al., "A Comparative-Study of Zeolite and Resin Adsorbents for the Separation of Fructose Glucose Mixtures," *Industrial & Engineering Chemistry Research*, vol. 26, No. 7, pp. 1407-1412 (Jul. 1987).

Hu, SQ. et al., "Conversion of fructose to 5-hydroxymethylfurfural using ionic liquids prepared from renewable materials." *Green Chemistry*, vol. 10, Issue 12, pp. 1280-1283 (Oct. 23, 2008).

Jianlong, W. et al., "Production of citric acid from molasses integrated with in-situ product separation by ion-exchange resin adsorption," *Bioresource Technology*, vol. 75, No. 3, pp. 231-234 (Dec. 2000).

Lee, K.N., "Continuous separation of glucose and fructose at high concentration using two-section simulated moving bed process," *Korean Journal of Chemical Engineering*, vol. 20, No. 3, pp. 532-537 (May 2003).

Navarro, A. et al., "Continuous chromatographic separation process: Simulated moving bed allowing simultaneous withdrawal of three fractions," Journal of Chromatography A, vol. 770, No. 12, pp. 39-50 (May 15, 1997).

Ortiz, A. et al., "Room temperature ionic liquid with silver salt as efficient reaction media for propylene/propane separation: Absorption equilibrium," *Separation and Purification Technology*, vol. 63, Issue 2, pp. 311-318 (Oct. 22, 2008).

Pedruzzi, I. et al., "Quantification of lactobionic acid and sorbitol from enzymatic reaction of fructose and lactose by high-performance liquid chromatography," *Journal of Chromatography A*, vol. 1145, Nos. 1-2, pp. 128-132 (Mar. 23, 2007).

Roden, L. et al., "Separation of Sugars by Ion-Exclusion Chromatography on a Cation-Exchange Resin," *Journal of Chromatography*, vol. 638, No. 1, pp. 29-34 (May 21, 1993).

Roman-Leshkov, Y. et al., "Phase modifiers promote efficient production of hydroxymethylfurfural from fructose," *Science*, vol. 312, No. 5782, pp. 1933-1937 (Jun. 30, 2006).

Staby, A. et al., "Comparison of chromatographic ion-exchange resins I. Strong anion-exchange resins," *Journal of Chromatography A*, vol. 897, Nos. 1-2, pp. 99-111 (Nov. 3, 2000).

Vente, J.A. et al., "Sorption and separation of sugars with adsorbents based on reversible chemical interaction," *Adsorption Science & Technology*, vol. 24, No. 9: pp. 771-780 (2006).

Yong, G. et al., "Efficient Catalytic System for the Selective Production of 5-Hhydroxymethylfurfural from Glucose and Fructose," *Angewandte Chemie-International Edition*, vol. 47, Issue 48, pp. 9345-9348 (Oct. 27, 2008).

ADSORPTION SEPARATION PROCESSES FOR IONIC LIQUID CATALYTIC PROCESSES

CROSS REFERENCE TO RELATED APPLICATION

This application claims the benefit of U.S. Provisional Patent Application No. 61/258,347, filed Nov. 5, 2009, which is hereby incorporated by reference in its entirety.

ACKNOWLEDGMENT OF GOVERNMENT SUPPORT

This invention was made with Government support under Contract DE-AC06-76RLO1830 awarded by the U.S. Department of Energy. The Government has certain rights in the invention.

FIELD

Disclosed are methods for separation of products, byproducts and ionic liquids from ionic liquid catalysis process reaction mixtures, and recycling of ionic liquids, particularly separation of mixtures from ionic liquid catalysis processes for the conversion of biomass, cellulose, and sugars into chemical intermediates, such as hydroxymethylfurfural.

BACKGROUND

Ionic liquids, due to their unique attributes, are a new generation of high performance solvents useful for catalytic and separation applications. Ionic liquid-based reactions are considered to be "green" compared to conventional solvents because they possess superior properties; they have relatively low vapor pressures, tend to be non-flammable or essentially non-combustible below their decomposition temperature, have excellent thermal stability with a wide range of tunable liquid properties, and are superior solvents for a diverse array of compounds. The ionic liquids' properties result in liquid carriers that provide operational flexibility and minimize the environmental footprint of a process.

For catalysis systems in ionic liquids, the ionic liquid can act as a solvent (liquid carrier) and/or as a catalyst to stabilize reaction intermediates. However, a major barrier hindering industrial use of ionic liquids is the high costs; the ionic liquid cost is often greater than the reaction product mixture and desired product cost itself. For a practical process, the ionic liquid should be recovered from the reaction mixture for re-use at a very high recovery rate (greater than 80% or 90% or most likely greater than 99 or 99.9%).

The separation technologies currently in use in such ionic liquid catalysis process systems are distillation, vacuum distillation or extraction. Those techniques provide low separation efficiency for many desired products, are not readily scalable to a commercial level, have an unacceptable effect on the environment, and/or are not safe for workers. In addition, certain of the currently used techniques require raising reaction mixtures to boiling temperatures and/or cooling the same-energy intensive activities harmful to the environment and costly on a commercial scale. In distillation processes the required heating levels of the reaction product mixture necessary to cause separation also result in many side reactions that are detrimental to recovery of product, feed, catalyst, and/or the ionic liquid. Extraction processes use particular organic solvents and apparatus that cause the process not only to be more complicated on a commercial scale (as opposed to lab bench processes) but also produce undesirable solvent waste.

Hydroxymethylfurfural (HMF) is a key intermediate chemical and is a flexible platform for producing chemicals and fuels that can substitute for today's petroleum-derived reaction product mixtures. Recent developments have been made in processes for the production of HMF on a commercial scale and at costs that allow petroleum reaction product mixture substitution in the production of major chemicals from biomass and biobased fuels. Scientists at Pacific Northwest National Laboratories have developed a number of inventions demonstrating catalytic conversion of sugars to HMF at high selectivities and conversions using a soluble catalyst in ionic liquid solvents. Such processes require a separation of unreacted sugars, HMF and ionic liquids.

Efficient, cost effective and environmentally sound separation processes for ionic liquid catalysis process systems are needed to recover important reaction components such as the ionic liquids as well as the reaction product and byproducts and allow for the recycling of the ionic liquid on a commercially economically and environmentally acceptable scale.

SUMMARY

Separation of product molecules from ionic liquid reaction mixtures has been a challenge for processes using ionic liquids as solvents (carriers) and/or catalysts. This is particularly true for HMF; due to the high boiling points of many of the useful ionic liquids and the instability of HMF and sugar at high temperatures, distillation separation is not a practical option in HMF generating processes. Separation of HMF by extraction encounters a lack of highly selective solvent and the formation of emulsion between the ionic liquids and extraction solvents. The existing conventional separation processes are not economically and/or environmentally acceptable on a commercial production scale. In addition, such conventional methods do not allow for the cost-effective and/or environmentally friendly recovery of the ionic liquid on a commercial-production scale. The presently disclosed adsorption separation processes utilize researched and developed adsorbent materials in a fixed structure. The ionic liquid reaction mixtures flow through a bed of particularly chosen adsorbent materials and the desired product molecule, such as HMF, is selectively retained by the adsorbent material while the costly ionic liquid solvent is eluted for re-use. The saturated adsorbent material is then regenerated (or desorbed) for recovery of the HMF. The presently disclosed processes allow such separations to be performed economically and in an environmentally sound manner, on a commercial production scale.

DETAILED DESCRIPTION

Figure 1:
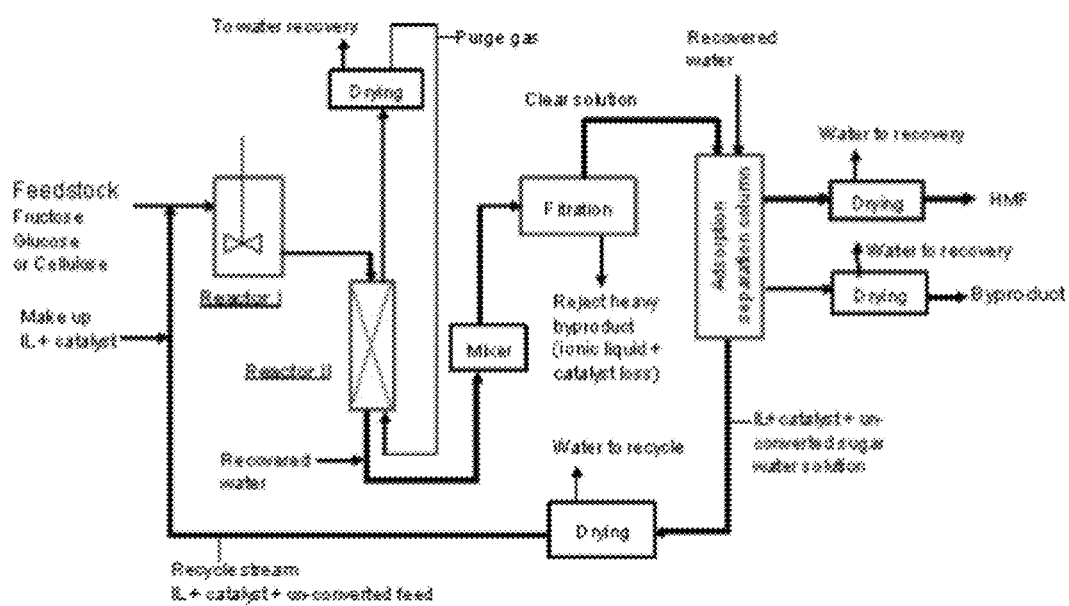
FIG. 1 is a process flow diagram for a virtually completely "green" continuous flow, ionic liquid-based catalytic process for production of HMF from low-cost sugar reaction product mixtures including embodiments of the presently disclosed adsorption processes.

Presently disclosed are methods for the separation of ionic liquid solvents and other ionic species in an ionic catalysis process reaction mixture by use of solid adsorbent materials, as well as the recycling and re-use of the ionic liquid solvents. A particularly chosen solid adsorbent material repels the ionic species while retaining different product molecules based on their differing affinities to the adsorbent material. More specifically, disclosed are methods for separation of ionic liquids and other ionic products from ionic liquid catalysis process reaction mixtures, particularly in conversion of biomass, cellulose, and sugars into chemical intermediates such as hydroxymethylfurfural (HMF). In certain embodiments the disclosed ionic liquid separation process comprises (i) mixing an ionic liquid-containing reaction mixture with de-ionized water to make a water solution mixture, (ii) flowing the water solution mixture into an adsorption column, (iii) collecting eluted separated ionic liquids and unreacted sugars, (iv) flushing the column with a regeneration fluid to desorb the production product, and (v) directly reusing the ionic liquids.

To understand the disclosed separation processes and apparatus, discussion of ionic liquid catalysis process development is presented. Inventors at the Pacific Northwest National Laboratory in Richland Wash. (a US Department of Energy government research laboratory) have invented and developed processes using ionic liquids as carriers for catalytic conversion of carbohydrate polymers into value-added chemicals such as HMF in the presence of a soluble catalyst, a breakthrough in catalysis chemistry of compounds such as HMF production with high product yield with an economically and environmentally acceptable levels when produced on a commercial scale. Specifically, as disclosed in U.S. application Ser. No. 12/110,997 (filed Apr. 28, 2008), which is incorporated herein by reference in its entirety, methods for the conversion of carbohydrate polymers in ionic liquids, including cellulose, that yield value-added chemicals such as glucose and HMF at temperatures below 120° C. are provided. Catalyst compositions that include various mixed metal halides are described that are selective for specified products with yields of up to 56% in a single step process. The processes include heating a carbohydrate polymer at a preselected temperature in an ionic liquid that includes a catalyst comprising a preselected ratio of at least two metal halides or metal salts for a time sufficient to convert the carbohydrate polymer to desired carbohydrate derivatives and products. Carbohydrate polymers include, but are not limited to, e.g., cellulose, hemicelluloses, cellobiose, maltodextrin, starch, or other selected carbohydrates. Reaction processes described herein employ ionic liquids as a reaction medium and various mixed metal halides as reaction catalysis. In the reaction medium, these mixed metal halides catalyze the necessary decrystallization and hydrolysis reactions for conversion of the carbohydrate polymers or parent polysaccharides to desired and/or value-added reaction products. In various embodiments, the mixed metal halide catalyst includes $CuCl_2$ and at least one other metal halide, e.g., $CrCl_2$, $CrCl_3$, $PdCl_2$, $FeCl_3$, $LaCl_3$, $NiCl_2$, $CoCl_2$, but is not limited thereto. The mixed metal halide catalyst includes at least two metal halides, or metal salts, with a first metal halide or metal salt comprising from 50% to 99% of the total moles of catalyst and a second metal halide or metal salt comprising from 50% to 1% of the total moles of catalyst. In another embodiment, the carbohydrate polymer is cellulose, the catalyst is a paired metal halide, e.g., [$CuCl_2$:$CrCl_2$], and the carbohydrate product includes HMF. In another embodiment, the carbohydrate product includes a carbohydrate monomer, e.g., glucose. In another embodiment, the carbohydrate product includes HMF. Temperatures and reaction times are selected to maximize the selected carbohydrate products and to minimize product degradation. Temperatures for conversion are preferably in the range from 100° C. to 180° C. More preferably, temperatures for conversion are below 120° C. Time to achieve conversion of carbohydrate polymers is preferably a time in the range from 0.01 hours to 8 hours, but is not limited.

Additional discoveries by inventors at the Pacific Northwest National Laboratory include the methods disclosed in U.S. application Ser. No. 11/774,036 (filed Jul. 6, 2007), which is also incorporated herein by reference in its entirety, include the use of ionic liquids for selective conversion of carbohydrates to value-added chemicals. In one method of the invention, selective conversion of a carbohydrate to value-added chemical(s) includes the steps of: mixing the carbohydrate up to a limit of solubility with an ionic liquid; heating the carbohydrate in the ionic liquid at a reaction temperature in the absence of added catalyst for a reaction time sufficient for conversion of the carbohydrate. Conversion of the carbohydrate produces furans at a substantial yield. Preferred ionic liquids used as solvents for conversion of carbohydrates have a chemical formula: 1-$R_1$-3-$R_2$-imidazolium chloride ([R$_1$R$_2$IM]Cl), where R$_1$ and R$_2$ are alkyl groups of formula (C$_x$H$_{2x+1}$) where X=1 to 18. In another embodiment, ionic liquids include a cation of chemical formula 1-R$_1$-3-R$_2$-imidazolium, where R$_1$ and R$_2$ are alkyl groups of formula (C$_x$H$_{2x+1}$) where X=1 to 18, and an anion. Anions include, but are not limited to, e.g., halides, sulfates, sulfonates, phosphates, acetates, phosphates, triflates, hexafluorophosphates, tetrafluoroborates, hexafluoroborates, and aluminum chloride. In another embodiment, the anion is methanesulfonate or trifluoromethanesulfonate. In other embodiments, the ionic liquid is 1-ethyl-3-methyl-imidazolium chloride ([EMIM]Cl) or 1-butyl-3-methyl-imidazolium chloride ([BMIM]Cl). In other embodiments, ionic liquids selected for use include pyridinium salts (e.g., N-alkylpyridinium salts), phosphonium salts (e.g., P,P,P,P-tetraalkylphosphoriium salts), and tetraalkylammonium salts (e.g., N,N,N,N-tetraalkylammonium salts) that include a stoichiometric quantity of a suitable anion, described herein. In yet other embodiments, carbohydrates including, e.g., monosaccharides (e.g., glucose, fructose, mannose, and galactose, and derivatives thereof, e.g., sorbitol, anhydrosorbitol), disaccharides (e.g., sucrose, maltose, lactose, cellobiose, and derivatives thereof), and polysaccharides (e.g., maltodextrins, starches, cellulose, and derivatives thereof) are converted in the absence of a co-solvent to value-added chemicals including, e.g., furfurals, e.g., 5-hydroxymethylfurfural (HMF). In other embodiments, 5-carbon sugars (e.g., arabinose, xylose, ribose, and lyxose) are converted to value-added chemicals including, e.g., furfural. In certain embodiments, 6-carbon sugars (e.g., glucose, fructose, mannose, and galactose) are converted to value-added chemicals, including, e.g., 5-hydroxymethylfurfurals. In other embodiments, a furan obtained from conversion of fructose by the process of the invention includes 5-hydroxymethylfurfural (HMF). In another embodiment, a furan is obtained in the absence of a catalyst. In other embodiments, fructose is converted to HMF in conjunction with a catalyst that is an acid. In other embodiments, fructose is converted to HMF with a catalyst that is a metal halide. Metal halides include, but are not limited to, e.g., AlCl$_3$, CrCl$_2$, CrCl$_3$, FeCl$_2$, FeCl$_3$, CuCl, CuBr, CuCl$_2$, CuBr$_2$, VCl$_3$, MoCl$_3$, PdCl$_2$, PtCl$_2$, PtCl$_4$, RuCl$_3$, RhCl$_3$, and combinations thereof.

Reaction times for conversion of carbohydrates vary, e.g., from 0.01 minutes to 300 minutes; or from 0.01 minutes to 30 minutes; or from 0.01 minutes to 5 minutes. Reaction temperatures for conversion of carbohydrates vary from 20° C. to 400° C.; or from 80° C. to 250° C.; or from 100° C. to 200° C. In one embodiment, fructose is converted to HMF at a reaction temperature of 80° C. and a reaction time of between 1 hour and 4 hours. In another embodiment, fructose is converted to HMF at a reaction temperature of 120° C. and a reaction time of 180 minutes. In another embodiment, reaction time and reaction temperature is between 1 hour and 3 hours at 120° C. In yet another embodiment, fructose is converted to HMF in 1-ethyl-3-methylimidazolium [EMIM] CH$_3$SO$_3$ to which methane sulfonate or its conjugate acid are added as a catalyst. Reaction temperature and reaction time are between 80° C. for 2 hours and 30° C. for 12 hours.

In another embodiment, conversion of fructose gives a yield of levulinic acid and α-angelicalactone below 1 percent by weight and more particularly below 0.1 percent by weight. In one embodiment, conversion of glucose to HMF proceeds at a reaction temperature of 100° C. and a reaction time of 3 hours. In another embodiment, conversion of glucose produces a furan that is furfural. In another embodiment, the carbohydrate converted is a sugar alcohol yielding a furan that is an anhydrosugar alcohol or a dianhydrosugar alcohol. In another embodiment, the sugar alcohol is sorbitol. In another embodiment, conversion of carbohydrates is achieved in a batch reactor or a batch reactor system. In other embodiments, conversion of carbohydrates is achieved in a continuous flow reactor or a continuous flow reactor system.

In still yet other embodiments, reaction times and reaction temperatures for conversion of carbohydrates are from 0.01 minutes at 400° C. to 10 hours at 20° C. Conversion of carbohydrates can also be achieved at reaction times of less than or equal to 0.01 minutes, e.g., in conjunction with a flash conversion process. Conversion of carbohydrates can include a reaction time of from 0.01 minutes to 5 hours and a reaction time of from 400° C. down to 20° C. In another embodiment, conversion of glucose to HMF includes a reaction time of from 0.01 minutes to 5 hours and a reaction time of from 400° C. down to 20° C. In another embodiment, conversion of carbohydrates is effected in a reaction time of 0.01 minutes, e.g., in conjunction with a flash conversion process. In another embodiment, carbohydrates are converted in a reaction time and a reaction temperature of between 0.01 minutes at 250° C. and 12 hours at 20° C. In various embodiments, conversion of carbohydrates is greater than or equal to 80 percent and yield of furans is greater than or equal to 50 percent on a mole basis; or at least 35 percent by weight. In another embodiment, conversion of glucose gives yields of levulinic acid and α-angelicalactone of less than 3 percent by weight.

The primary barrier to using HMF in high-volume chemical and fuel applications is its high-production cost and correspondingly low availability. To be commercially viable, HMF must be produced on a large scale at a cost comparable to petroleum-derived reaction product mixtures such as para-xylene (PX) and terephthalic acid (PTA). The development of the above-discussed novel continuous flow, ionic liquid-based catalytic processes for production of HMF from low-cost sugar reaction product mixtures are better understood with reference to FIG. 1. The process includes two major processes and apparatus, the above described catalytic reactions and the presently disclosed separation processes.

A reaction product mixture is mixed with (recycled) catalyst/ionic liquid stream in a stirrer reactor (I), to completely dissolve reaction product mixture in the ionic liquid and initiate reaction. The mixture moves to a plug flow reactor (II) to achieve high single-pass conversion with good control of process conditions. The HMF product is reactive, so the effluent of the reactor II is quenched by water to a lower temperature. At this stage, insoluble and particulate byproducts are rejected by filtration or centrifugation.

The clear solution containing HMF, catalyst, ionic liquid and unreacted sugars are then separated using an embodiment of the presently disclosed adsorbent separation processes wherein a moderate temperature adsorption column (e.g., 20-200° C. or 20-100° C. or 20-80° C. or 20-60° C.) is utilized, where HMF and HMF byproducts are retained, while passing the catalyst, ionic liquids and un-converted sugars (to then be re-used) at differing elution times. The adsorbent is optimized to maximize HMF capacity and selectivity. HMF and its byproducts are then desorbed sequentially with a flow stream such as water or other solvents and the desorbed streams each dried to produce chemically pure HMF product and HMF byproduct. The ionic liquid stream is dried and sent to Reactor I for immediate re-use.

In certain embodiments water is continuously used and recovered and re-used to minimize waste. Various drying processes can remove water from the different process streams, including spray drying, pervaporation, absorption, or adsorption. Since three water molecules are produced with conversion of each sugar molecule, a purge gas stream such as nitrogen strips moisture from Reactor II. Water vapor in the purge gas can be condensed out for recovery and the purge gas re-used. A purge gas may also enhance mixing and mass transport.

The properties of ionic liquids are utilized to produce the surprisingly superior performance of the disclosed separation processes. The term "ionic liquid" is commonly used in reference to salts whose melting point is relatively low (below 100° C.). Ionic liquid-based reactions are considered to be "green," compared to conventional solvents, because they possess superior properties including having extremely low vapor pressures, are non-flammable or essentially non-combustible below their decomposition temperature, have excellent thermal stability with a wide range of tunable liquid properties, and are superior solvents for a diverse array of compounds.

A major challenge for the commercial-scale ionic liquid-based catalytic processes is the high cost of ionic liquids relative to conventional solvents. Since the ionic liquid is used as the solvent (and at times as the catalyst as well), a major constituent in the reaction mixture, its material cost has a direct impact on the overall process cost and thus the cost of the desired end product, such as HMF. To overcome this challenge, the disclosed processes recycle and re-use the ionic liquids with minimal loss and simple process steps for the re-use. The disclosed processes allow for immediate or nearly immediate recycling and re-use of the ionic liquids without the need for intermediate steps to treat the ionic liquids to put them in condition for re-use. This enables the ionic liquids to be used as working capital analogous to a solid catalyst in heterogeneous catalytic processes, rather than as a consumable like a traditional solvent in current processes. Ionic liquid recycling relies on effective separation of the ionic liquid from the reaction products. The feasibility of the high-performance ion-exclusion adsorptive separation processes disclosed herein, in an economic, environmentally-sound manner, on a commercial scale, is evidenced by the example processes test results disclosed herein.

The cost of the separation process itself is also an important factor in the cost of producing HMF commercially because it is a major component of both capital and operating costs. Separation of the water extract of the reacted product mixture is an important cost-saving step. To complete the process recycle loop, however, other separation steps, such as rejection of the heavier and polymeric byproducts, removal of water from HMF, removal of water from the catalyst/solvent/ionic liquid, is also disclosed and the efficacies in an economic manner on a commercial scale are demonstrated by the disclosed example test results.

Figure 15:
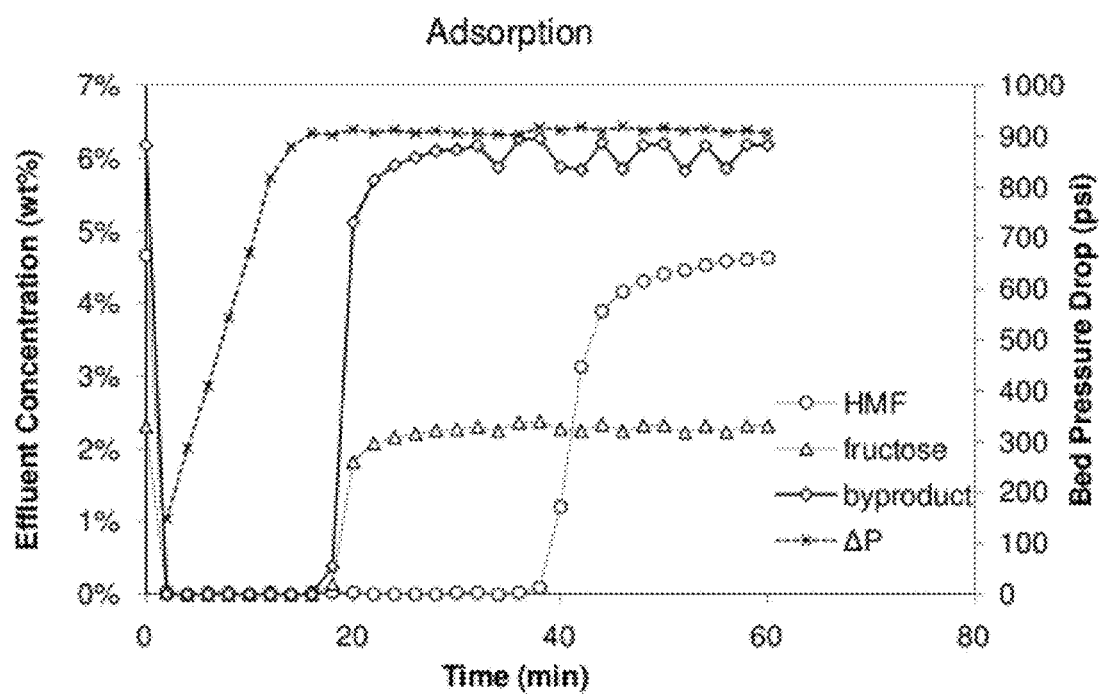
FIG. 15 is a graph showing adsorbent materials breakthrough curves of HMF, fructose and byproducts, under selected conditions.
Figure 16:
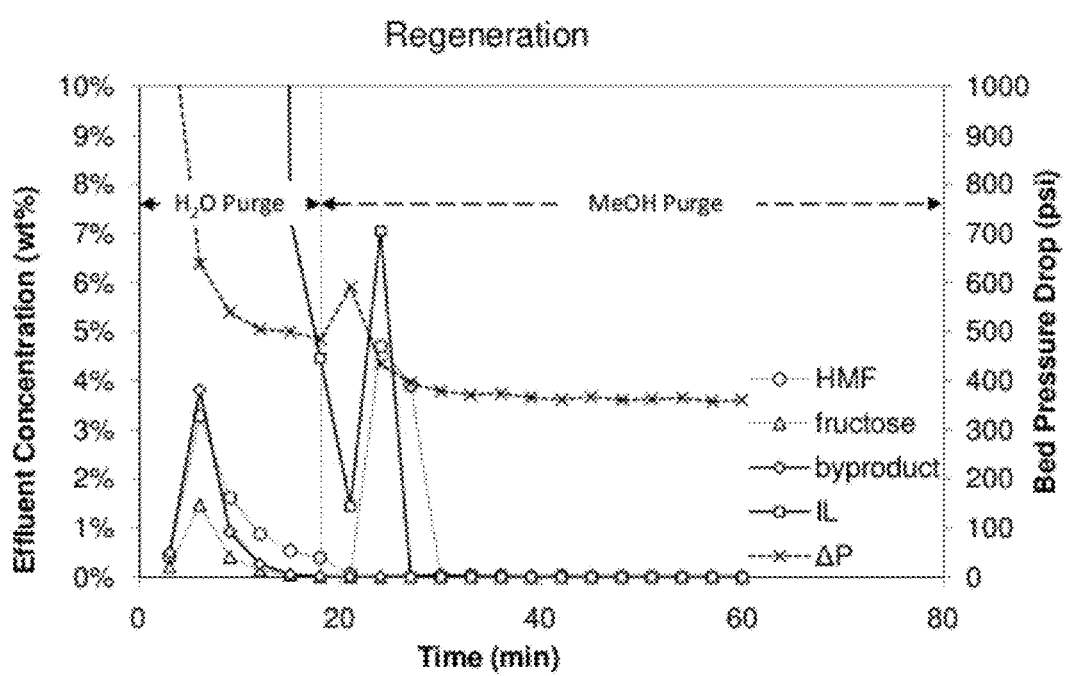
FIG. 16 is a graph showing adsorbent materials' regeneration profiles of HMF, fructose and byproducts, under selected conditions.

The presently disclosed separation processes provide a complete or virtually complete separation route for production of concentrated HMF and for up to at least 90% or 80% or 70% or 60% or 50% recovery of the catalyst and/or the ionic liquid. Such recovery can be seen in, e.g., in Example 7, where the ionic liquid recovery was 99.4%. The presently disclosed adsorption separation processes enable high recovery by selective rejection of the ionic liquids and unreacted sugars (and catalysts used) over the adsorbent material. As shown in FIGS. 15 and 16, sugar and ionic liquid elute first during the adsorption process, while HMF is being retained by the adsorbent material. An ionic liquid profile is measured during regeneration rather than during an adsorption process because the ionic liquid concentration is more dilute and thus more readily determined during regeneration of the column as compared to during the adsorption process. However, as shown in FIGS. 15 and 16, the sorbent bed pressure drop profile during adsorption provides a manner to determine ionic liquid breakthrough time since the ionic liquid is of significantly higher viscosity than the regeneration solvent (methanol in this example) that was initially present in the column during adsorption. Accordingly, the pressure profile during adsorption can be considered as surrogate for an ionic liquid breakthrough curve. FIGS. 15 and 16 include such pressure profiles as well as an ionic liquid breakthrough profile in FIG. 16. High-level recovery may be realized in part by thorough washing of the adsorbent column and repeated separation/recycling of residual solution mixtures. In large-scale (commercial-scale) operations the recovery percentage level will be dictated by process economics. The efficient separation processes disclosed herein are vital to lower HMF commercial-scale production costs and provide better, more efficient, environmentally sound commercial-scale separation processes that recover the catalysts and/or ionic liquids for re-use, allow for the collection of unreacted sugars to be re-processed, and to separate the predetermined reaction product(s).

In certain embodiments, the disclosed separation by adsorption processes were found to provide superior separation of HMF from other species. The catalysts and ionic liquid solvents exist as ions in a liquid state or in a water solution. By controlling them during the reaction and/or separation process, and the pH and adsorbent material properties, the catalysts and/or ionic liquids can pass through the adsorption column without significant retention, while HMF and other byproducts are trapped (adsorbed) on the adsorbent material and later desorbed with a flushing fluid, e.g., water. The adsorbent properties and separation conditions are carefully determined so that unconverted (unreacted) sugar is eluted separately from the catalysts and/or ionic liquids. To ensure unreacted sugars are eluted separately, appropriate adsorbent and separation conditions (e.g., 20 to 150° C. and a contact time with the adsorbent of from 1 second to a few hours) are selected such that sugars are only weakly adsorbed whereas HMF is strongly adsorbed. First, the ionic fluids flow through the column without significant retention. By flowing fluid such as water through a loaded column, unreacted sugars, which are weakly retained by the column adsorbent, are flushed through the column. Next, methanol or other solvent, is flowed through the column to desorb HMF. The ionic liquids and unreacted sugars are recycled back to the reactor to increase the HMF yield, saving on costs of the ionic liquids, and to avoid having unreacted sugar impurities in the HMF product or in waste streams.

Ionic Liquids In general, the ionic liquids separated in the currently disclosed processes may comprise the catalysis reaction solvent (carrier) and/or may act as a reaction catalyst. Embodiments of the ionic liquids of the presently disclosed processes preferably are in the liquid phase with relatively low viscosities when undergoing large-scale (commercial production scale) separation/adsorption processes conducted at a temperature range of 20° C. to 200° C. The ionic liquid melting temperature in certain embodiments is preferably below 80° C. or below 50° C. or even lower, such as room temperature, with a viscosity under adsorption conditions of less than 20 Poise. While the low melting point and low viscosity are desirable physical properties from the standpoint of fluid transport and mixing, the choice of an ionic liquid is largely determined by its catalytic reaction activity. In certain embodiments, solvents, such as water, are added to the ionic liquid to reduce the viscosity.

Particularly useful ionic liquids separable by the currently disclosed methods are imidazolium or phosphonium-based ionic liquids. The cation head group is either an imidazolium or a phosphonium ion. The side chains on the cation head group are alkyl functional groups of the formula $C_nH_{2n+1}$ where n=1 to 18. The anions belong to a group that includes, but are not limited to, e.g., halides, sulfates, sulfonates, phosphates, acetates, phosphates, triflates, hexafluorophosphates, tetrafluoroborates, hexafluoroborates, and aluminum chloride. In another embodiment, the anion is methanesulfonate or trifluoromethanesulfonate. In certain embodiments the ionic liquid separation process includes separation of an ionic liquid comprising 1-ethyl-3-methyl-imidazolium chloride ([EMIM]Cl) or 1-butyl-3-methyl-imidazolium chloride ([BMIM]Cl). In other embodiments, the disclosed separation processes include separation of ionic liquids comprising pyridinium salts (e.g., N-alkylpyridinium salts), phosphonium salts (e.g., P,P,P,P-tetraalkylphosphoriium salts), and tetraalkylammonium salts (e.g., N,N,N,N-tetraalkylammonium salts) that include a stoichiometric quantity of a suitable anion, described above. In certain of the disclosed separation processes, the separated ionic liquid comprises or triisobutyl (methyl) phosphonium tosylate (also referred to herein as CYPHOS 106). [EMIN]Cl or Cyphos 106 act as both catalysts and solvents for HMF production, such as for fructose conversion to HMF.

Catalysts: When the ionic liquid does not act as the catalyst, other reaction catalysis reaction mixtures separated using the currently disclosed separation methods may include catalysts (in addition to the ionic liquid solvents) such as various mixed metal halides. In the reaction medium, these mixed metal halides catalyze the necessary decrystallization and hydrolysis reactions for conversion of the carbohydrate polymers or parent polysaccharides to desired and/or value-added reaction products. In various embodiments, the mixed metal halide catalyst includes $CuCl_2$ and at least one other metal halide, e.g., $CrCl_2$, $CrCl_3$, $PdCl_2$, $FeCl_3$, $LaCl_3$, $NiCl_2$, $CoCl_2$, but is not limited thereto. The mixed metal halide catalyst includes at least two metal halides, or metal salts, with a first metal halide or metal salt comprising from 50% to 99% of the total moles of catalyst and a second metal halide or metal salt comprising from 50% to 1% of the total moles of catalyst.

HMF: Hydroxymethylfurfural (HMF) is an important potential "carbon-neutral" reaction product mixture for fuels and chemicals that can substitute for petroleum-derived reaction product mixtures. The presently disclosed processes act to separate HMF product (and/or C5-C6 molecules of an aromatic-ring type compounds, and/or a derivative of HMF, or mixtures thereof) from ionic liquid catalysis reaction product mixtures including separating, for example, the HMF product, unreacted sugar(s), ionic liquid(s), catalyst(s), HMF-like molecules, HMF derivatives or molecules of aromatic-ring type of structures, and reaction intermediates and byproducts.

Unreacted Sugars: Ionic liquid catalysis reaction product mixtures separated using the currently disclosed processes may include unreacted sugars when making HMF. The following unreacted sugars may be present in the reaction product mixture, fructose and glucose in percentages of from 0.01% to 10 wt % or 0.01% to 5 wt % or 0.01% to 3 wt %. Certain of the unreacted sugars could be only partially dehydrogenated or dehydrated sugars, undesirable byproducts.

HMF production ionic liquid catalysis reaction product mixtures (or ionic liquid catalysis reaction product mixtures): The reaction product mixtures separated by the disclosed HMF separation processes are ionic liquid catalysis reaction product mixtures from a catalytic conversion process using ionic liquid solvents and sugar feeds. The ionic liquid catalysis reaction product mixtures may include, e.g., the following components in the following percentage ranges: HMF from 0.1 to 80% and a likely percentage range of 0.5% to 30%; ionic liquid comprising CYPHOS 106 from 0.1% to 99% and a likely percentage range of 20% to 95% or ionic liquid comprising [EMIN]Cl from 0.1% to 99% and a likely percentage range of 20% to 95%; catalysts from 0.01% to 5% and a likely percentage range of 0.1% to 1%; unreacted fructose from 0.01% to 30% and a likely percentage range of 0.1% to 10% or unreacted glucose from 0.01% to 30% and a likely percentage range of 0.1% to 10%.

Adsorbent Materials: Adsorbent materials used in the presently disclosed processes preferably include one or more of the following characteristics: (i) high adsorption capacity to HMF, preferably greater than 5 wt %, (ii) I adsorption capacity to sugar molecules such as glucose or fructose, preferably less than 5 wt %, (iii) retention of the ionic liquid, preferably less than 5 wt %, (iv) a high partition coefficient, preferably greater than 1.5 and (v) high recovery of HMF after washing, preferably greater than 50% or 60% or 70% or 80% or 90% or 99% (percent of HMF recovered in the washing solution from the total amount that was adsorbed on the adsorbent). The partition coefficient can be determined using the below formula, which measures relative concentration of species i to species j in the solid phase from the mobile phase.

$$\alpha_{ij} = \frac{\left(\frac{C_i}{C_j}\right)_{solid}}{\left(\frac{C_i}{C_j}\right)_{Mobile}}$$

The adsorbent materials may comprise one or more of the following: carbon or carbon black (pores formed between small (a few to tens of nanometer) carbon particles, while the carbon particle itself is nearly dense), MCM-41 (mesoporous silica), porous silica, NaY zeolite (zeolite is microporous, aluminosilicate minerals), 13X zeolite, organophilic zeolite, activated charcoal, porous graphitized carbon black (Carbopack X), Spherical C18 bonded flash silica (octadecyl-functionalized porous silica), phenyl-functionalized silica gel, macroreticular non-ionic resin of polystyrene crosslinked with divinylbenzene (Amberlite XAD-1180), octadecyl-functionalized spherical silica) (PLC-18), Amberlyst 16 Wet (strong acid cation exchange resin in the hydrogen form with a poplystyrene-divinlybenzene gel matrix and sulfonate functional groups), Carboxen 1012 (carbon molecular sieve of a surface area approximately 1500 $m^2/g$ and mesoproporosity from 15-21 Å pores), zeolyst molecular sieve (H-mordenite zeolite), Pinnacle II phenyl bulk packing (phenyl-functionalized silica gel), Carboxen 1003 (carbon molecular sieve of a surface area approximately 1000 $m^2/g$ and largely microporosity from 5-8 Å pores), Carboxen 1021 (carbon molecular sieve of a surface area approximately 600 $m^2/g$ and microporosity from 5-8 Å pores), DWNTs (double-walled carbon nanotubes), synthetic hydrotalcite, Pinnacle II amino bulk packing, Pinnacle II cyano bulk packing, BCR-704 (molecular sieve 1.0), Dowex Monosphere 99Ca/320 (strong acid cation exchange resin in the calcium form with a poplystyrene-divinlybenzene gel matrix and sulfonate functional groups), mesoproroussilicalite-1, nano-silicalite-1, HY, NaY, CsNaY 2IE, CsY 1IE, CsY 3IE, ZSM-5 $SiO_2/Al_2O_3$=50:1 (aluminosilicate zeolite mineral belonging to the pentasil family of zeolites), ZSM-5 $SiO_2/Al_2O_3$=100:1, NH4 ZSM-5, Carboxen 569 (carbon molecular sieve of a surface area approximately 485 $m^2/g$ and microporosity from 5-8 Å pores), Carboxen 1018 (carbon molecular sieve of a surface area approximately 675 $m^2/g$ and microporosity from 6-8 Å pores), Carbosieve S-III (carbon molecular sieve with a surface area approximately 975 m²/g and primarily microporosity of 4-11 Å pores), Carbosieve G (carbon molecular sieve of a surface area approximately 1160 m²/g and primarily microporosity from 6-15 Å pores), Carboxen 1000 (carbon molecular sieve with a surface area approximately 1200 m²/g and micro- and mesoporosity from 10-20 Å pores), Carboxen 1016 (carbon molecular sieve with a surface area approximately 75 m²/g and primarily mesoporosity).

The adsorbent materials preferably include one or more of the following physical characteristics:

(a) surface areas of from 1 mg²/g to 3000 mg²/g or from 50 mg²/g to 3000 mg²/g or from 200 mg²/g to 1000 mg²/g or greater than 500 mg²/g;

(b) pore volume of from 0.1 cm³/g to 5.0 cm³/g or from 0.1 cm³/g to 2.0 cm³/g or from 0.25 cm³/g to 1.0 cm³/g;

(c) mean pore diameter of from 0.1 nm to 1000 nm or from 0.1 nm to 20 nm or from 0.4 nm to 5 nm or from 1 nm to 5 nm;

(d) average particle size of from 0.1 μm to 5000 μm or from 0.1 μm to 3000 μm or from 100 μm to 3000 μm.

Reaction Product Mixture to Adsorbent Material Ratios: The preferred reaction product mixture liquid to adsorbent material weight ratio may depend on the actual reaction product mixture composition, such as the type of ionic liquid and percentage of HMF to ionic liquid and type of unreacted sugars present, as well as the adsorbent materials being used in a particular process. However, in general, preferable liquid to solid weight ratio (based on adsorbent dry weight) have been found to be greater than 1:1, or greater than 4:1, or greater than 10:1 (the liquid to solid ratio is preferably as high as possible, but is determined by the adsorbent capacity and concentration of HMF in the ionic liquid).

The separation processes can be used with a variety of apparatus depending on what is best for the actual commercial process. Embodiments of the processes and apparatus include use of suitable process configurations, such as fluidized beds, moving beds, simulated moving beds, continuous countercurrent moving-beds, adsorption/desorption packed columns and the like. The adsorbent material can be made into different engineered forms for loading into respective adsorption apparatus. Examples, of the engineered adsorbent structures are spheres of diameter from 100 μm to about 3 mm, extrudate of diameter from 1 to 3 mm and length from 2 to 5 mm, and structured beds of adsorbent loading thickness from 50 μm to 2 mm. See Tables 1 and 2 below for specific adsorbent materials and their specified physical characteristics.

In certain embodiments of the disclosed separation processes an adsorption column is packed with solid adsorbent material, such as those discussed above, e.g., resins of different pore structures and surface chemistries, activated carbons, zeolites, metal oxides, or other suitable adsorbents for the compounds requiring separation. The adsorbent materials have surface charges that repel the ionic liquid, unreacted sugars and/or ionic catalyst, while retaining different product molecules having different affinities for the adsorbent material. The ionic liquid and unreacted sugars typically elute from the adsorption column first and are collected and re-used, while the adsorbed molecules having the differing adsorption affinities elute at different times from the saturated column. As a result, the reaction mixture is separated into the desired product fractions and re-usable fractions.

After the ionic liquid reaction takes place the reaction product mixture may directly be separated with the present adsorption process by maintaining the reaction product mixture in a state of liquid fluid or the reaction product mixture can be diluted by addition of solvent to modify its properties such that the optimum adsorption performance can be achieved. For example, the product mixture can be diluted with water to lower its viscosity, reduce pressure drop across the adsorbent bed, and enhance the molecular diffusion rate from the bulk fluid into the adsorbent pores. Depending upon the specific solid adsorbent materials, surface charge of the adsorbent particles can further be controlled by adjusting the pH of the mixture fluid.

Reaction product mixture (in either the liquid fluid state or as a diluted mixture) is introduced to the column and flowed through the column at a liquid-hourly space velocity ("LHSV") of 0.1 to 100 v/v/h or 2 to 50 v/v/h). The adsorption process is operated at relatively low temperatures, typically operating at 20 to 200° C., or 20 to 150° C. or 20 to 100° C. or 20 to 80° C. or 20 to 60° C. or 50 to 60° C. or 60 to 80° C.—making the disclosed separation processes more economical on a commercial scale, less environmentally damaging, and allowing for a safer work environment than existing separation processes used for ionic liquid catalysis process mixtures. The column may be operated isothermally near or above ambient temperature. A heat exchanger jacket and/or feed preheater may be used to maintain a relatively constant column temperature.

In certain embodiments of the disclosed methods the following process conditions to conduct adsorption can be utilized: column temperature ranges of 20 to 200° C., preferably, 25 to 120° C., or 40 to 80° C., or 40 to 60° C.; an adsorbent material loading in the adsorption bed of 50 to 1000 Kg/m³; a pressure drop for the fluid to flow through the adsorbent bed of from 0.1 to 100 bar, preferably, 0.1 to 5 bar, for moving the reaction product mixture through a commercial scale column; a liquid-hourly space velocity, that is, fluid-volume flow rate divided by the adsorbent bed volume of from 1 to 100 v/v/h through the column. As used herein, the "column temperature" means the temperature of the solid adsorbent material in the column. The liquid feed temperature may be different from the solid adsorbent temperature. However, the liquid temperature typically is the same or close to the solid adsorbent temperature upon its contact with the solid adsorbent. When the adsorption process is conducted on a commercial scale using a large adsorbent bed, there may be some temperature variation at different locations of the adsorption bed due to the heat of adsorption during the process. The adsorption temperature is preferably reasonably maintained over such a range that the feed mixture is maintained in the liquid phase inside the adsorption bed. The adsorbent bed may be dry or may be presoaked with solvent prior to introduction of the reaction product mixture.

As the reaction product mixture flows through the column different components of the reaction product mixture are either retained temporarily and elute sequentially on their own or are retained by and later flushed through the column. The ionic liquid elutes first together with the catalyst if a catalyst is added into the reaction product mixture. Elution of unreacted sugar follows the ionic liquid. As the unreacted sugars, such as glucose and fructose, and ionic liquid are eluting from the adsorbent bed, HMF is captured (adsorbed) by the adsorbent material. When HMF elution appears, the adsorbent bed is saturated. The retained HMF is recovered by regenerating the saturated adsorbent material.

Figure 2:
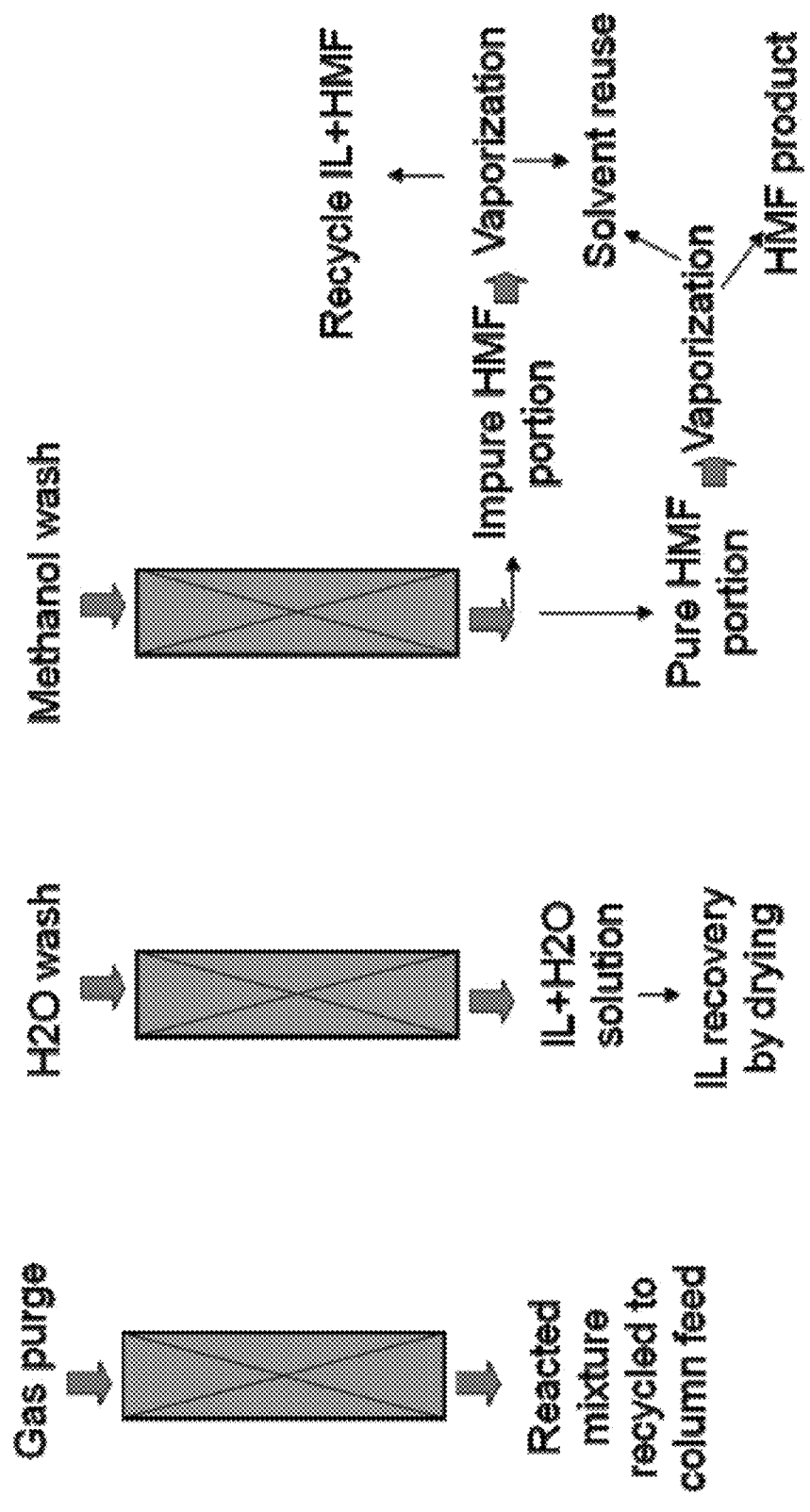
FIG. 2 illustrates certain apparatus useful for practicing the disclosed separation and regeneration processes.

After the adsorption step and before a solvent rinse step to recover adsorbed HMF, residual reaction product mixture trapped in interstitial spaces between adsorbent particles may be removed. In addition, weakly adsorbed sugars and sugar-like reaction intermediates and byproducts are also desorbed (and removed/recycled) to produce maximum purity HMF. The adsorbent material may be regenerated as shown in the illustrated process in FIG. 2. FIG. 2 illustrates a column regeneration process scheme wherein the column is purged by a gas flow, inert gases such as nitrogen or compressed air ("Gas Purge"), and the resulting liquid mixture may then be recycled back to the feed during the adsorption process.

In one embodiment of the disclosed process, the adsorbent material is regenerated by removing any reaction product mixture trapped inside voids of the packed bed, removing any reaction product mixture trapped inside catalyst pores, and desorbing adsorbed HMF. The removal steps produce a residual reaction product mixture that can be recycled back to the adsorption step. Desorption releases concentrated HMF for product recovery.

Water can be used to wash trapped reaction product mixture as well as weakly adsorbed sugars out of the column. At the end of the water wash, the water can be blown out of the column using high pressure nitrogen or like means. Methanol can be used in the final wash step to elute HMF adhered to the adsorbent. HMF product is then isolated from the HMF/methanol solution. Any organic solvent of low boiling point and relatively low cost such as methanol, ethanol, isopropanol, ethyl acetate and the like may be used for the desorption of HMF. A water volume of five to eight bed volume of water may be utilized—the bed volume is the volume of adsorbent material packed in the column. Effluent samples from the column can be analyzed by HPLC to determine HMF concentration. Specific examples of the separation processes are disclosed below for illustrative purposes only—not to be construed as restrictive of the scope of the claims.

Two liquid portions (an impure HMF portion and a pure HMF portion) are generated from the methanol flushing step. The first portion (impure HMF portion) is a mixture of HMF, ionic liquid, and solvent. The HMF and ionic liquid can be recovered from this mixture by removing the solvent by, e.g., vaporization and recycled back to the reaction product mixture of the adsorption process step, while the solvent is also recovered for re-use. The second liquid portion comprises pure HMF, which can be used for recovery of HMF product and solvent.

In other embodiments, the separation process apparatus may be directly coupled to the ionic liquid HMF production catalysis system, such as shown in FIG. 1. Specifically, continuous flow, ionic liquid-based catalytic processes for production of HMF from low-cost sugar reaction product mixtures are performed using two major processes and apparatus, the above described catalytic reactions and apparatus and the presently disclosed separation processes and corresponding apparatus.

Figure 3:
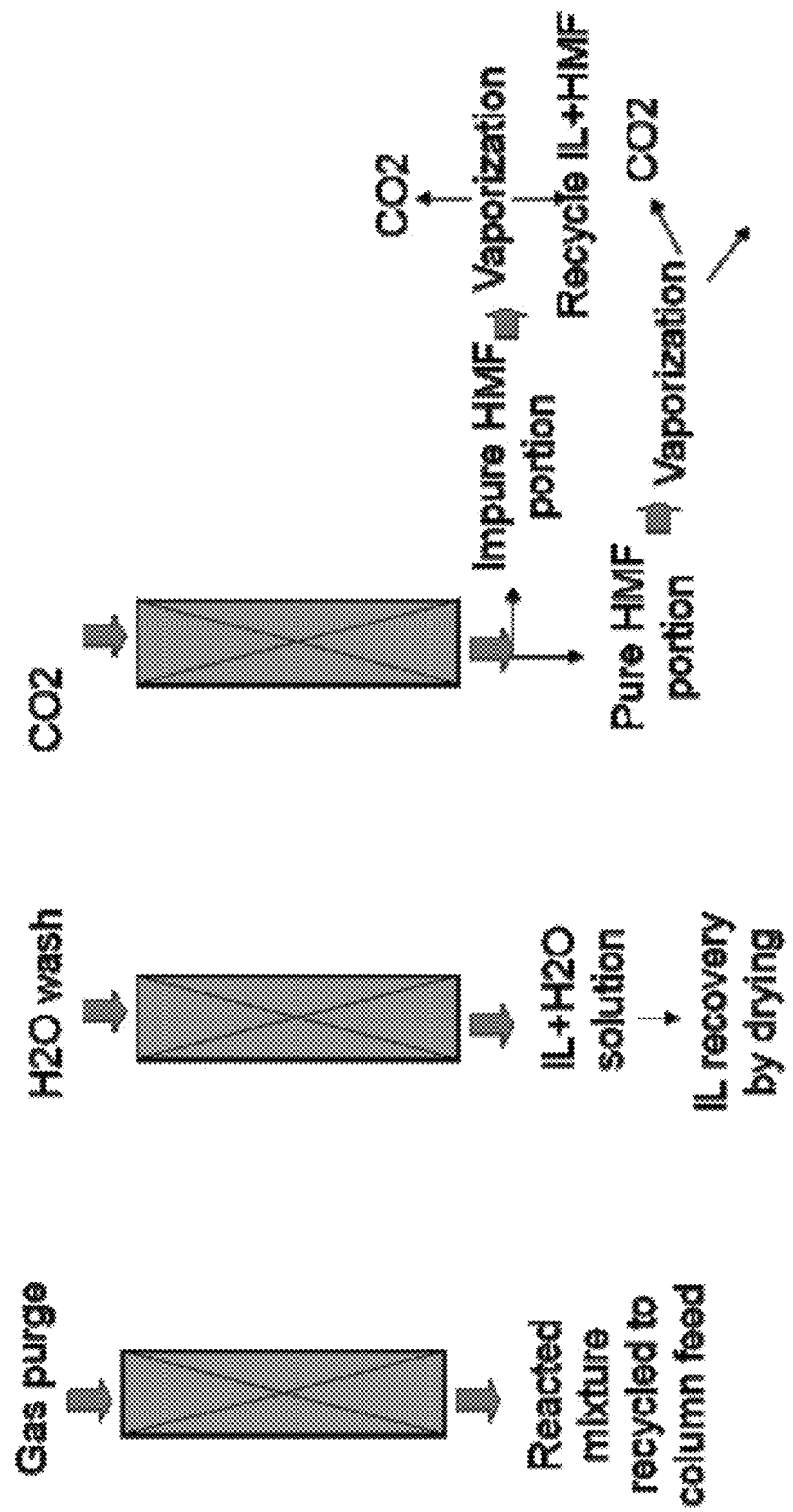
FIG. 3 illustrates certain apparatus useful for practicing the disclosed regeneration processes for regenerating a saturated adsorbent material bed.

With reference to FIG. 3, the same basic process as discussed in connection with FIG. 1 is used but no organic solvents are utilized. Instead, the regeneration of the saturated adsorbent column is carried out completely by use of a gas purge, such as use of supercritical $CO_2$. Thus, the gas purge of the column is followed by the water flush ("$H_2O$ Wash") and a supercritical $CO_2$ purge.

Figure 4:
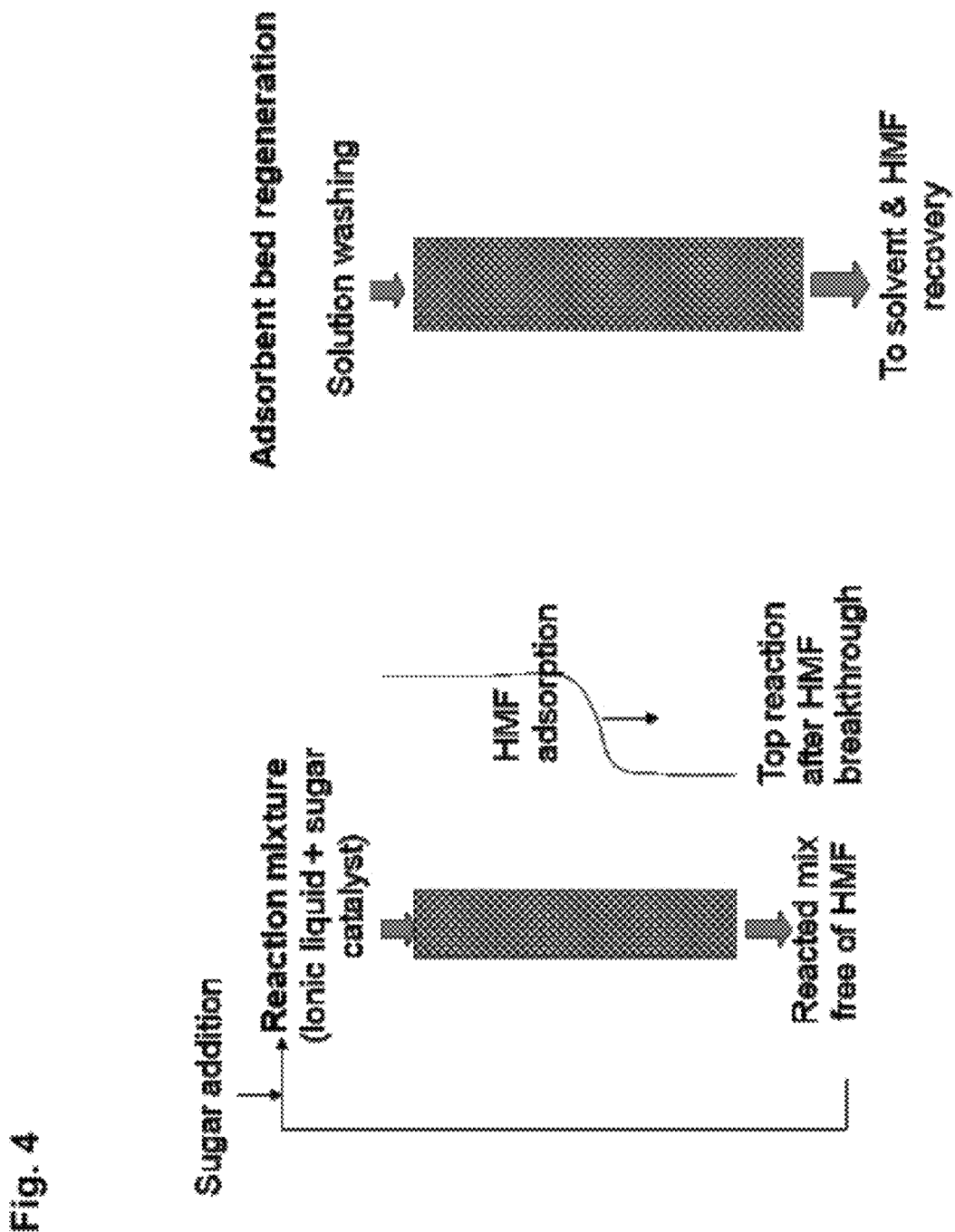
FIG. 4 illustrates apparatus for an embodiment of the disclosed separation process that is integrated directly with an HMF ionic liquid catalytic production process.

With reference to FIG. 4, in another embodiment, the HMF product is adsorbed during the ionic liquid catalysis reaction. Sugar is added to a mixture of ionic liquid and a catalyst to form the reaction product mixture that is then passed through the adsorbent column. A reaction mixture free of HMF product and HMF byproduct is eluted from the column. The HMF product is retained by the adsorbent material in the column as soon as the HMF product is produced by the reaction. Once the adsorption column is saturated the bed is regenerated to recover the HMF product and HMF byproducts as described above.

Figure 5:
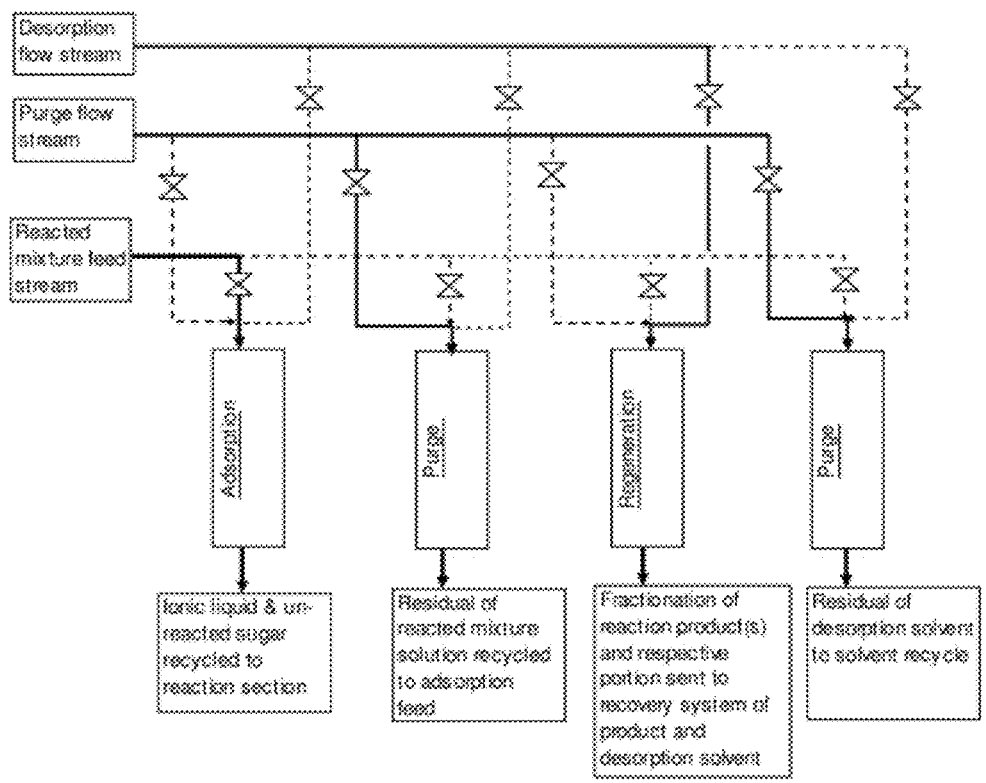
FIG. 5 is a process schematic of an embodiment of the disclosed adsorption separation process using a multi-bed system for industrial-scale production of HMF.

In certain embodiments the processes are particularly well suited for industrial scale operation. In certain of the disclosed adsorption processes, multiple adsorption beds are used to conduct adsorption, purge, and regeneration processing simultaneously to have a continuous or semi-continuous production process. The continuous process provides high productivity, low energy consumption and superior quality control. As illustrated in FIG. 5, as the reacted liquid product mixture passes through a fresh adsorption bed, the ionic liquid solvent and unconverted sugars are passed through the beds, while HMF is adsorbed on the adsorbent bed. When the adsorbent column is fully saturated with HMF, the reacted liquid product mixture is switched to feed into the next fresh adsorbent material column. The saturation of the adsorbent column can be determined by monitoring the liquid compositions between the inlet and outlet of the adsorbent column. Column bed saturation is reached if the inlet and outlet compositions are relatively similar in HMF concentration levels.

The saturated column may then be purged through use of an inert gas and water to remove any residual liquid product mixture trapped in void spaces of an adsorbent column. Collected solution from the saturated column may be cycled back to an adsorption column inlet for re-adsorption. Regeneration is conducted by passing a volatile liquid stream such as alcohol through the column at or above the adsorption temperature. HMF is desorbed from the adsorbent column and collected regeneration effluent solution is vaporized. The HMF product and alcohol is separated and recovered from the liquid phase and vapor phase, respectively. After regeneration, the adsorbent bed is purged again by use of an inert gas and/or water to recover the alcohol and fully rejuvenate the adsorbent column. The adsorption, purge, regeneration, purge, adsorption cycle can be repeated by switching valving and fluid flow control.

Figure 6A:
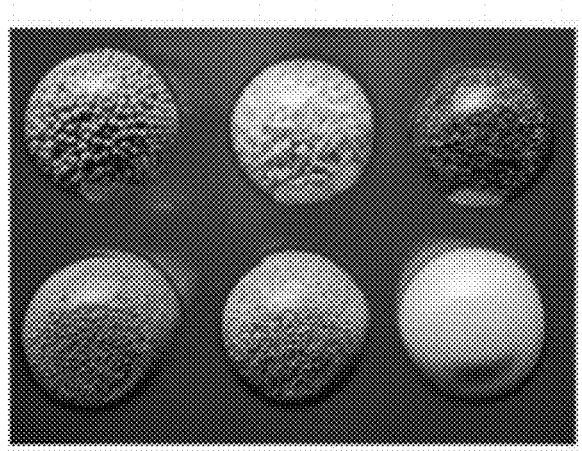
FIGS. 6a and 6b are photographs of adsorption particles engineered for use in embodiments of the disclosed separation processes, showing (a) the morphology of the particles and (b) the micro-structures of the particles.
Figure 6B:
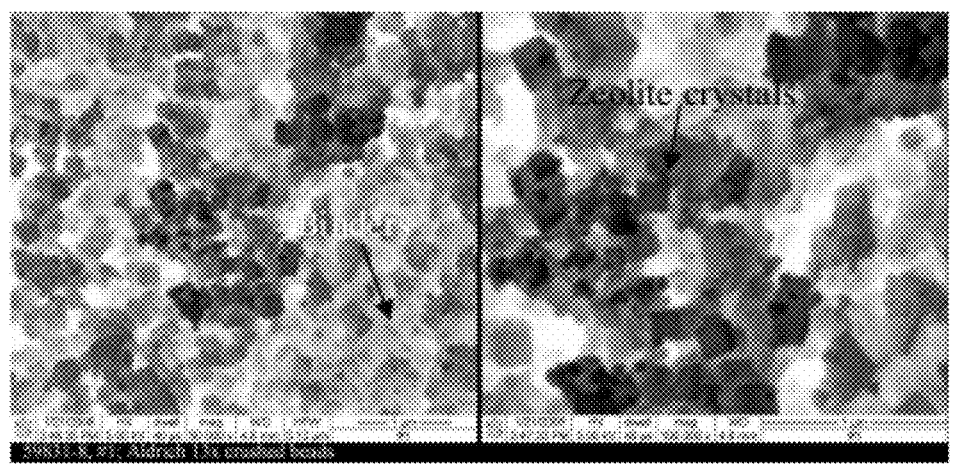

In certain embodiments particularly suited for large-scale production of HMF, the adsorbent material is prepared in forms suitable for an industrial adsorption process. The zeolite powder of crystal sizes from tens of nanometers to a few micrometers is combined with one or more binders, such as alumina colloidal solution, silica colloidal solution, and polymer solution, to form a slurry or paste. Adsorbent material having particles of differing shapes and/or sizes may be formed accordingly. For example, adsorbent materials having particles of cylindrical shape may be formed by extrusion of the paste; adsorbent materials having small spherical particles may be made by atomizing or spray drying of a paste or slurry. The resulting particles may be calcined at certain temperatures to enhance the mechanical strength of the adsorbent material. FIGS. 6a and 6b show certain adsorbent material particle shapes suitable for use in an industrial adsorption processes. Individual zeolite crystals having such engineered particles are visible using SEM photography. Without the use of one or more binders, the particles of the adsorbent materials tend to form a loose powder. The amount of binder used is preferably as little as possible because addition of binder adds to cost and occupies adsorbent bed volume. The binder content is typically from 5 to 50%, preferably 5 to 30% of the total particle weight.

Mechanical strength of the engineered particle may be used to aid the industrial adsorption process. In a fixed adsorbent bed particles should be strong enough to withstand the large pressure gradient between the flow inlet and outlet. For fluidized bed operation, the particles should be strong enough to withstand attrition due to constant particle movement and collision.

Pressure drop from the adsorption column (or bed) inlet to the outlet is an important design dimension for large-scale adsorption separation processes for ionic liquid fluids. Ionic liquids are relatively viscous, for example, the ionic liquid used in many of the Examples of this invention has viscosity at 60° C. of about two hundred times the viscosity of water at 20° C. For a particle-packed adsorption bed, the pressure drop can be calculated using the following Ergun equation:

$$\frac{\Delta P}{L} = 150 \cdot \frac{\mu(1-\varepsilon)^2 U}{\varepsilon^3 \cdot d_p^2} + 1.75 \cdot \frac{\rho(1-\varepsilon)U^2}{\varepsilon^3 \cdot d_p}$$

ΔP=pressure drop across a randomly-packed particle bed, bar
L=length of packed bed, m
μ=viscosity of fluid, Pa·s
ε=void fraction
U=superficial linear velocity, m/s
dp=size of the particle, m
ρ=density of fluid, kg/m3

Certain disclosed design dimensions of a particle-packed adsorption beds for an industrial-scale adsorption process for, e.g., 100,000 T per year of fructose to HMF processing capacity are listed in the process design table below. When flowing a substantially pure ionic liquid through the column. As used herein, "pure ionic liquid" means that the ionic liquid does not contain a substantial or affecting amount of particulates, polymers, and/or humins, the pressure drop is about 4.0 bars for an adsorbent bed of 4.0 m diameter and 4.8 m in height and being loaded with 3 mm diameter adsorbent particles. From the point of view of mass transport of HMF from the bulk fluid into the adsorbent particle, a smaller particle diameter is preferable less than 1 mm. From the point of view of the pressure drop, larger particle sizes are preferable, such as greater than 3 mm. A relatively high-pressure drop is associated with high energy consumption, high cost of the adsorption column or vessel, and stringent requirements for the mechanical strength of the particles. The process design table below illustrates a process design calculation of a pellet-loaded adsorption column for a commercial-scale plant having a processing capacity of 100 K tons of fructose to HMF per year (with a loading of fructose in an ionic liquid of 10 wt %, 10 wt % of HMF adsorption capacity).

| Process Design for an Embodiment of a Particle-Packed Adsorption Bed | |
|---|---|
| Composition of reacted liquid product mixture | |
| Glucose, wt % | 0.04 |
| Fructose, wt % | 0.09 |
| Formic acid | 0.00 |
| Levulinic acid | 0.00 |
| HMF, wt. % | 5.54 |
| Reaction intermediate, wt % | 1.12 |
| Ionic liquid, wt % | 93.21 |
| Fluid properties at 60° C. | |
| Fluid density, Kg/m³ | 1000 |
| Viscosity, kg/(m*s) or Pa*s | 0.2 |
| Volume flow rate, m³/h | 112.5 |
| Adsorption breakthrough time, min | 30 |
| LHSV, 1/h | 1.85 |
| Adsorbent bed | |
| Particle size, mm | 3 |
| Void fraction | 0.35 |
| Binder fraction | 0.1 |
| Adsorbent fraction | 0.55 |
| Adsorbent loading, T | 33.5 |
| Bed volume, m³ | 60.8 |
| Hydrodynamics | |
| Diameter of bed, m | 4 |
| Cross-sectional area, m² | 12.6 |
| Height of bed, m | 4.8 |
| Superficial linear velocity, m/s | 0.002 |
| Reynolds Number | 0.037 |
| Pressure drop, Bar/m | 0.82 |
| Total pressure drop, bar | 3.96 |

Figure 7:
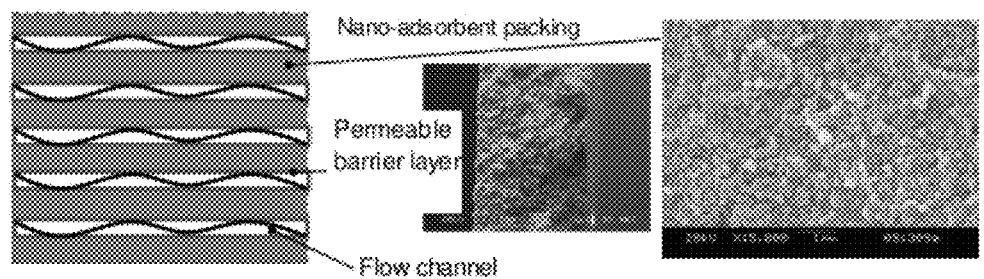
FIG. 7 illustrates a structured-adsorption bed used in certain embodiments of the disclosed separation processes.

In another embodiment, the adsorbent material vessel comprises a structured bed. An embodiment of such a structured bed is illustrated in FIG. 7, with the adsorbent vessel comprising an array of straight flow channels throughout the packed adsorbent material. The small adsorbent particles such as nano-zeolite crystals are sandwiched between porous barrier layers, such as porous metal, porous Teflon®, porous ceramic, porous ceramic/polymeric composite, and the like. The porous barrier layer fixes the nano-adsorbent particles and allows the separation mixture molecules to diffuse across. This embodiment may allow the adsorbent material slurry to be used without the addition of binders to keep the nano-particles together. This particular embodiment decouples channel flow hydrodynamics from the diffusion into the adsorbent particles. The channel spacing, thickness of the porous barrier layer, and thickness of the packed nano-particle layer are independent design parameters. Channel spacing may be, e.g., from 0.3 mm to 3 mm, the thickness of the barrier layer may be, e.g., from 0.025 mm to 0.30 mm, and the thickness of the nano-particle layer may be, e.g., from 0.3 mm to 3.0 mm. The thickness of the porous barrier layer should be as small as possible relative to the thickness of the nano-particle layer, such as less than 1 mm, and preferably less than 0.2 mm. The external mass transfer rate and pressure drop can be controlled by the channel spacing, while the diffusion rate into the adsorbent can be controlled by the thickness of the packed adsorbent layer. The structured bed embodiment allows for a lower pressure drop at smaller channel spacing than certain particle-bead-loaded adsorbent vessels.

As listed in the table below, for the same capacity and liquid product properties as used in the process design table above, the pressure drop is 1.5 bar for the structured bed embodiment, much lower than that for the 3 mm bead-packed bed embodiment. The structured bed vessel may have a diameter of 3 m and height of 8.3 m, providing a higher aspect ratio (length/diameter) than the bead-packed bed embodiment. The higher aspect ratio is generally preferred to achieve a plug flow pattern. In addition, an adsorbent packing thickness of 1 mm in the structured bed embodiment is much smaller than a 3 mm of the adsorbent bead, allowing for a much lower mass transfer resistance for molecules to diffuse into the adsorbent material.

The pressure drop of the structured bed embodiment can be calculated by the following equation:

$$\Delta P = f \cdot 4 \cdot \frac{L}{d_h} \cdot \left(\frac{1}{2} \cdot \rho \cdot U^2\right)$$

ΔP=pressure drop though a channel, bar
f=friction coefficient

L=length of channel length, m
dh=hydraulic diameter of the channel, m
U=superficial linear velocity inside channel, m/s
ρ=density of fluid, kg/m³

$$Re = \frac{\rho \cdot d_h \cdot U}{\mu}$$

$$f = \frac{16}{Re}$$

Re=Reynolds number
μ=viscosity of fluid, Pa·s
U=superficial linear velocity, m/s
dh=hydraulic diameter of the channel, m
ρ=density of fluid, kg/m3

The process design table below illustrates a process design calculation of an embodiment of the disclosed structured adsorption bed for a commercial HMF production plant having a processing capacity of 100 K ton of fructose to HMF per year (loading of fructose in ionic liquid of 10 wt. %, 10 wt % of HMF adsorption capacity).

| Process Design for an Embodiment of a Structured-Adsorption Bed | |
| --- | --- |
| Composition of reacted liquid product mixture | |
| Glucose, wt % | 0.04 |
| Fructose, wt % | 0.09 |
| Formic acid | 0.00 |
| Levulinic acid | 0.00 |
| HMF, wt. % | 5.54 |
| Reaction intermediate, wt % | 1.12 |
| Ionic liquid, wt % | 93.21 |
| Fluid properties at 60° C. | |
| Fluid density, Kg/m³ | 1000 |
| viscosity, kg/(m*s) or Pa*s | 0.2 |
| Volume flow rate, m³/h | 112.5 |
| Adsorption breakthrough time, min | 30 |
| LHSV, 1/h | 1.92 |
| Structured bed | |
| Flow channel spacer spacing, m | 0.01 |
| Flow channel opening, m | 0.001 |
| Adsorbent thickness, m | 0.001 |
| Inert layer thickness, m | 0.0001 |
| Nominal unit bed thickness, m | 0.0021 |
| Channel fraction | 0.476 |
| Binder fraction | 0.048 |
| Adsorbent fraction | 0.476 |
| Adsorbent loading, T | 33.5 |
| Bed volume, m³ | 58.6 |
| Hydrodynamics | |
| Diameter of bed, m | 3.0 |
| Cross-sectional area, m² | 7.1 |
| Height of bed, m | 8.3 |
| Superficial velocity inside channel, m/s | 0.0093 |
| Hydraulic diameter of channel, m | 0.0018 |
| Re | 0.1 |
| Pressure drop, bar | 1.5 |

Figure 8:
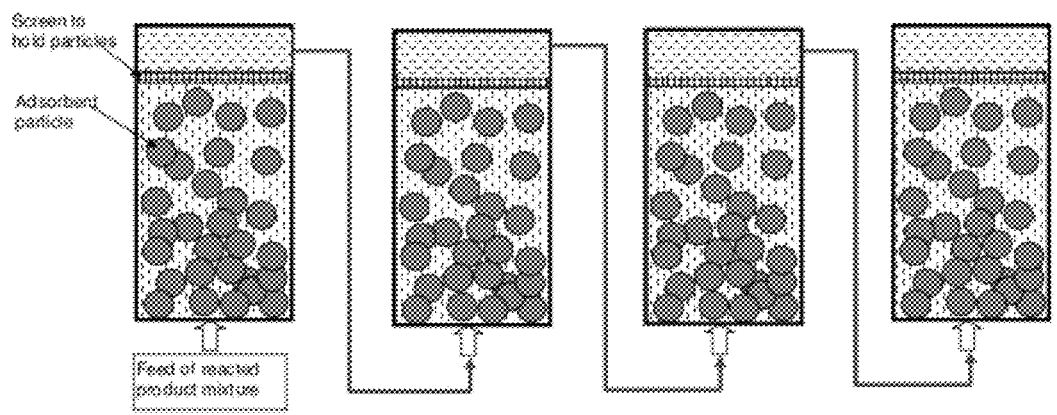
FIG. 8 is a process schematic of an embodiment of the disclosed adsorption separation process using a multi-stage fluidized adsorption bed system for industrial-scale production of HMF.

In other embodiments of the disclosed separation process, commercial-scaled fluidized adsorption beds or vessels may be used, where the adsorbent material is fixed inside the adsorption vessel and liquid/solid contacting and adsorption/desorption is performed. As illustrated in FIG. 8, adsorbent material particles move around from the pressure exerted by the feed liquid mixture as it enters the adsorption vessel. Adsorbent bed particles in a first adsorbent material particle bed or vessel are retained inside the bed by a separator as the liquid flow exits the vessel. The solid/liquid separator may comprise any suitable separation device, such as a mesh screen, a cyclone, sedimentation, and/or centrifugation. The liquid flow from the first adsorbent material particle bed can move to a second adsorbent vessel for further adsorption/separation. When the first adsorbent bed is saturated, the liquid feed mixture flow is moved to another adsorbent material bed while the first adsorbent bed is regenerated.

The fluidized bed embodiment provides an advantageously, relatively low, pressure drop and has the flexibility of utilizing adsorbent materials of relatively small diameter. The fluidized bed embodiment also provides superior liquid/solid mixing capabilities, which in turn allows rapid washing of the saturated solid. As shown in the table below the pressure drop for an embodiment of the fluidized bed is only 0.4 bar for a commercial HMF production plant having the same capacity and fluid properties as shown in the two tables above. The pressure drop for an upward fluidized bed can be calculated as follows:

$$\Delta P = (1-\epsilon) \cdot \rho_P \cdot g \cdot L$$

ΔP=pressure drop across a fluidized bed, bar
ε=liquid fraction of the bed
L=height of the fluidized bed, m
g=constant, 9.8 m/s²
$\rho_P$=density of adsorbent particle, kg/m³

Illustrated in the process design table below is a process design calculation of an embodiment of the disclosed separation process using a fluidized adsorption bed for a commercial plant of processing capacity of 100K ton of fructose to HMF per year (loading of fructose in ionic liquid of 10 wt. %, 10 wt % of HMF adsorption capacity).

| Process Design for an Embodiment of a Fluidized Adsorption Bed | |
| --- | --- |
| Adsorbent bed | |
| pellet size, mm | 0.20 |
| void fraction | 0.55 |
| Binder fraction | 0.05 |
| Adsorbent fraction | 0.40 |
| Adsorbent loading, T | 33.5 |
| Bed volume, m³ | 83.6 |
| Hydrodynamics | |
| Diameter of bed, m | 4 |
| Cross-sectional area, m² | 12.6 |
| Height of bed, m | 6.7 |
| Superficial velocity, m/s | 0.002 |
| Total pressure drop, bar | 0.40 |

EXAMPLES

Embodiments of adsorbent materials useful for the disclosed processes for separating HMF, ionic liquids, unreacted sugars and other components of the ionic liquid catalysis reaction product mixtures were tested. Particular adsorbent materials for the selective adsorption of HMF over unreacted sugars, such as fructose and glucose, in ionic liquid mixtures, are disclosed. Certain embodiments utilizing particular adsorbent materials were tested, such as zeolite series adsorbent materials (Z), Carbon series adsorbent materials (C), Silica series adsorbent materials (S), and Polymeric resin series adsorbent materials (R). Particular suitable adsorbent materials and their relevant properties are shown in Table 1 and Table 2.

TABLE 1

| Sample ID | Generic Name | Label Name | Source |
|---|---|---|---|
| C1 | Activated Carbon | Granular Activated Charcoal | Sigma-Aldrich |
| C2 | Activated Carbon | Carbon | |
| C3 | Graphitized Carbon Black | Ketjen Black | Degussa |
| C4 | Graphitized Carbon Black | Carbopack X | Supelco/Sigma-Aldrich |
| C5 | Carbon Molecular Sieve | Carboxen 1021 | Sigma-Aldrich |
| C6 | Carbon Molecular Sieve | Carboxen 1003 | Sigma-Aldrich |
| C7 | Carbon Molecular Sieve | Carboxen 1012 | Sigma-Aldrich |
| C8 | Multiwall Carbon Nanotubes | MWNTs | NanoAmor |
| C9 | Carbon Molecular Sieve | Carboxen 569 | Sigma-Aldrich |
| C10 | Carbon Molecular Sieve | Carboxen 1018 | Sigma-Aldrich |
| C11 | Carbon Molecular Sieve | Carbosieve S-III | Sigma-Aldrich |
| C12 | Carbon Molecular Sieve | Carbosieve G | Sigma-Aldrich |
| C13 | Carbon Molecular Sieve | Carboxen 1000 | Sigma-Aldrich |
| C14 | Carbon Molecular Sieve | Carboxen 1016 | Sigma-Aldrich |
| C15 | Double-Wall Carbon Nanotubes | DWNTs | CNI |
| Z1 | Zeolite NaY | NaY Zeolite | Sigma-Aldrich |
| Z2 | Zeolite 13X | 13X Zeolite | Sigma-Aldrich |
| Z3 | Zeolite Silicalite-1 | Organophilic Molecular Sieve | Sigma-Aldrich |
| Z4 | Zeolite H Mordenite | Zeolyst Molecular Sieve | Zeolyst International |
| Z5 | Zeolite Faujasite | BCR-704 (molecular sieve 1.0) | EU Reference Materials |
| Z6 | Zeolite Silicalite-1 | Meso Silicalite-1 | synthesized by hydrothermal growth in porous carbon template |
| Z7 | Zeolite Silicalite-1 | Nano Silicalite-1 | |
| Z8 | Zeolite HY | HY(SiO2/Al2O3 = 80:1) | Zeolyst |
| Z10 | Zeolite CsNaY | CsNaY 2IE | two-time ion exchange of Z1 with CsNO$_3$ solution |
| Z11 | Zeolite CsY | CsY 1IE | one-time ion exchange of Z8 with CsNO$_3$ solution |
| Z12 | Zeolite CsY | CsY 3IE | thre -time ion exchange of Z8 with CsNO$_3$ solution |
| Z13 | Zeolite ZSM-5 | HZSM-5 (SiO2/Al2O3 = 50:1) | synthesized by a self-assembly flow reactor method |
| Z14 | Zeolite ZSM-5 | HZSM-5 (SiO2/Al2O3 = 100:1) | synthesized by a self-assembly flow reactor method |
| Z15 | Zeolite NH4 ZSM-5 | NH4 ZSM-5 (SiO2/Al2O3 = 80:1) | Zeolyst |
| Z16 | | Silicate | |
| S1 | Mesoporous Silica | MCM-41 | Mobil |
| S2 | Porous Silica | Porous Silica | Steward Environmental Solutions |
| S3 | Octadecyl-Functionalized Silca | Spherical C18 bonded flash silica | Supelco/Sigma-Aldrich |
| S4 | Phenyl-Functionalized Silica | Phenyl-Functionalized Silica Gel | Sigma-Aldrich |
| S5 | Cyano Functionalized Silica | Pinnacle II Cyano Bulk Packing | Restek |
| S6 | Amino Functionalized Silica | Pinnacle II Amino Bulk Packing | Restek |
| S7 | Phenyl Functionalized Silica | Pinnacle II Phenyl Bulk Packing | Restek |
| H1 | Hydrotalcite | Synthetic Hydrotalcite | Sigma-Aldrich |
| R1 | Macroreticular Polystyrene DVB | Amberlite XAD-1180 | Rohm Haas/Sigma-Aldrich |
| R2 | Octadecyl-Functionalized Silca | PLC-18 | Supelco/Sigma-Aldrich |
| R3 | Cation Exchange Resin H Form | Amberlyst 16 Wet | Rohm Haas/Sigma-Aldrich |
| R4 | Cation Exchange Resin Ca Form | Dowex Monosphere 99Ca/320 | Dow Chemical/Sigma-Aldrich |

TABLE 2

Properties of Adsorbents for Certain Embodiments of the Separation Processes

| Sample ID | Surface Area [m$^2$/g] | Pore Volume [cm$^3$/g] | Pore Diameter [Å] | Particle Size [μm] | Mesh Size | Specific Gravity | Apparent Density [g/cm$^3$] | Moisture Level [wt %] |
|---|---|---|---|---|---|---|---|---|
| C1 | 1600 | | | | 4/14 | | | |
| C2 | 1070 | | | | | | | |
| C3 | 2600 | 7.651 | 22.17~150 | | | 1.8 | 0.115 | |
| C4 | 240 | 0.62 | 100 | | 60/80 | 0.41 | | |
| C5 | 600 | 0.3 | 5~8 | | | | 0.62 | |
| C6 | 1000 | 0.92 | 5~8 | | 40/60 | | 0.46 | |
| C7 | 1500 | 0.66 | 19~21 | | 80/120 | | 0.5 | |
| C8 | 112 | | | | | | | |
| C9 | 485 | 0.44 | 5~8 | | 20/45 | | 0.58 | |
| C10 | 675 | 0.35 | 6~8 | | | | 0.6 | |
| C11 | 975 | 0.39 | 4~11 | | 60/80 | | 0.61 | |
| C12 | 1160 | 0.51 | 6~15 | | 60/80 | | NA | |
| C13 | 1200 | 0.85 | 10~12 | | 60/80 | | 0.48 | |
| C14 | 75 | 0.34 | | | 60/80 | | 0.4 | |
| C15 | 633.9 | | | | | | | |
| Z1 | 900-1000 | | 7.5-8.5 | Powder* | | | | |
| Z2 | 900-1000 | | 7.5-8.5 | Powder* | | | | |
| Z3 | 300-400 | | 5.4-5.8 | Powder* | | | | |

TABLE 2-continued

Properties of Adsorbents for Certain Embodiments of the Separation Processes

| Sample ID | Surface Area [m²/g] | Pore Volume [cm³/g] | Pore Diameter [Å] | Particle Size [μm] | Mesh Size | Specific Gravity | Apparent Density [g/cm³] | Moisture Level [wt %] |
|---|---|---|---|---|---|---|---|---|
| Z4 | 400-700 | | 6.0-7.0 | Powder* | | | | |
| Z5 | 586.9 | | 6.68 | | | | | |
| Z6 | 300-400 | | 5.4-5.8 | Powder* | | | | |
| Z7 | 300-400 | | 5.4-5.8 | Powder* | | | | |
| Z8 | 700 | | 2.4 | Powder* | | | | |
| Z10 | 900-1000 | | 7.5-8.5 | Powder* | | | | |
| Z11 | 900-1000 | | 7.5-8.5 | Powder* | | | | |
| Z12 | 900-1000 | | 7.5-8.5 | Powder* | | | | |
| Z13 | 300-400 | | 5.4-5.8 | Powder* | | | | |
| Z14 | 300-400 | | 5.4-5.8 | Powder* | | | | |
| Z15 | 300-400 | | 5.4-5.8 | Powder* | | | | |
| Z16 | | | | Powder* | | | | |
| S1 | 806 | 0.7~1 | 35 | | 4/14 | | | |
| S2 | 449 | | | | | | | |
| S3 | | | 70 | | | | | |
| S4 | 500 | | 60 | | 200/400 | | | |
| S5 | | | | 5 | | | | |
| S6 | | | | 5 | | | | |
| S7 | | | | 5 | | | | |
| H1 | 80-100 | | | <5 | | 2.0 | | 0.35% |
| R1 | 500 | 1.4 | 400 | 534 | 20/60 | 1.01 | 0.69 | 66% |
| R2 | 180 | | | 12 | | | | |
| R3 | 30 | 0.2 | 250 | 700 | | | 0.78 | 50% |
| R4 | | | | 320 | | | | 59% |

*Zeolite loose powder comprising agglomerates of zeolite crystals of sizes from tens of nm to a few μm.

Example 1

Adsorption Separation of HMF and Imidazolium Ionic Liquid

Embodiments of adsorbent materials' selectivity for selectively adsorbing HMF over monosaccharides such as glucose in an imidazolium based ionic liquid. Samples of solid adsorbent materials were contacted with a liquid mixture containing the imidazolium ionic liquid [EMIM]Cl (1-ethyl-3-methyl imidazolium chloride), HMF, a monosaccharide (fructose or glucose), and levulinic acid (LA) in the presence or absence of water at 80° C. under air seal at atmospheric pressure. The sample was shaken at 700 rpm for 1 hour to enhance mixing of the powder with the liquid. Each adsorbent material was tested under the same conditions with three feed liquid mixtures. Feed liquid mixture A had a nominal composition of 1% glucose, 0.5% levulinic acid, 3.5% HMF, and 95% [EMIR/]Cl by mass. Feed liquid mixture B had a nominal composition of 1% fructose, 0.5% levulinic acid, 3.5% HMF, and 95% [EMIM]Cl by mass. Feed liquid mixture C had a nominal composition of 0.5% fructose, 0.25% levulinic acid, 1.75% HMF, 50% water, and 47.5% [EMIM]Cl by mass. The liquid to solid mass ratio varied over the range of 2 to 15 depending on the density of the adsorbent tested while the solid loose packing volume to liquid volume ratio was 1. When adsorption was complete the bulk liquid phase diluted with water and separated from the solid adsorbent by centrifuge-aided filtration for 30 minutes at 2000 rpm. This liquid phase and the feed liquid mixture were both analyzed using a HPLC system equipped with a BioRad HPX-97C Ca ion column and a refractive index detector. Component adsorption capacities were calculated from the change in the liquid compositions.

Adsorption capabilities of the following adsorbent materials are shown in Tables 3-5: C1 and C2 (activated carbon), C3 and C4 (graphitized carbon black), S1 (mesoporous silica), S2 (porous silica), S3 and R2 (octadecyl-functionalized porous silica), S4 (phenyl-functionalized silica gel), R1 (macroreticular non-ionic resin of polystyrene crosslinked with divinylbenzene), R3 (strong acid cation exchange resin in the hydrogen form with a poplystyrene-divinylbenzene gel matrix and sulfonate functional groups), Z1 (NaY zeolite), Z2 (13X zeolite), and Z3 (organic philic zeolite).

Carbon black C3, activated carbon C1, and polymer resin R1 showed good adsorption capacity for HMF from the ionic liquid mixtures. Because the amount of solvent (ionic liquid and water) uptake by the adsorbent was not quantified due to the difficulty of performing an in-situ centrifuge at 80° C. to separate bulk liquid phase from the solid adsorbent, the mass balance for the minor components is not precise. Table 3 reports the separation data for [EMIM]Cl ionic liquid containing HMF, glucose, and levulinic acid, and indicates that activated or graphitized carbon black having the C1 or C3 physical characteristics, respectively, as shown in Table 2, and macrometicular polystyrene DVB, having the physical characteristics of R1 shown in Table 2 are particularly useful for embodiments of the disclosed separation processes.

Table 4 reports the separation data for [EMIM]Cl ionic liquid containing HMF, fructose, and levulinic acid and indicates that activated or graphitized carbon black having the C1 or C3 physical characteristics, respectively, as shown in Table 2, macrometicular polystyrene DVB, having the physical characteristics of R1 shown in Table 2, and zeolite silicalite-1 having the physical characteristics of Z3 shown in Table 2, are particularly useful for embodiments of the disclosed separation processes.

Table 5 reports the separation data for [EMIM]Cl ionic liquid containing HMF, fructose, levulinic acid and water, and indicates that activated or graphitized carbon black having the C1 or C3 physical characteristics, respectively, as shown in Table 2, and phenyl-functionalized silica, having the physical characteristics of S4 shown in Table 2, are particularly useful for embodiments of the separation processes.

TABLE 3

Feed A: 1% Glucose, 0.5% LA, 3.5% HMF, 95% IL

| Short Name | Liq/Solid Ratio [g/g] | Glucose Uptake [g/g solid] | LA Uptake [g/g solid] | HMF Uptake [g/g solid] |
|---|---|---|---|---|
| C2 | 2.1 | −0.3% | 0.0% | 0.1% |
| C3 | 10.1 | −0.8% | 1.3% | 23.2% |
| S1 | 9.3 | −1.2% | 0.2% | 0.7% |
| S2 | 10.8 | −2.6% | −0.2% | −1.6% |
| Z1 | 4.2 | −1.0% | −0.1% | −0.2% |
| Z2 | 4.2 | −0.7% | −0.2% | 0.7% |
| Z3 | 4.2 | −1.2% | 1.0% | 5.5% |
| C1 | 8.3 | −0.6% | 1.3% | 9.1% |
| C4 | 4.8 | −0.6% | 0.3% | 3.1% |
| S3 | 3.7 | −0.3% | 0.3% | 1.8% |
| S4 | 3.6 | −0.6% | 0.2% | 1.6% |
| R1 | 3.8 | 0.1% | 0.7% | 8.5% |
| R2 | 4.8 | −0.4% | 0.3% | 2.2% |
| R3 | 3.7 | 0.7% | 0.2% | 2.8% |

TABLE 4

Feed B: 1% Fructose, 0.5% LA, 3.5% HMF, 95% IL

| Short Name | Liq/Solid Ratio [g/g] | Fructose Uptake [g/g solid] | LA Uptake [g/g solid] | HMF Uptake [g/g solid] |
|---|---|---|---|---|
| C2 | 2.1 | −0.2% | 0.0% | −0.3% |
| C3 | 10.6 | 10.0% | 0.8% | 19.5% |
| S1 | 9.6 | 2.9% | −0.2% | −2.9% |
| S2 | 10.4 | −2.1% | −0.4% | −1.6% |
| Z1 | 4.2 | −0.6% | −0.2% | −0.3% |
| Z2 | 4.2 | 0.1% | −0.3% | 1.1% |
| Z3 | 4.2 | −1.1% | 0.6% | 7.2% |
| C1 | 7.4 | 0.0% | 1.2% | 8.6% |
| C4 | 4.7 | 5.4% | 0.5% | 1.2% |
| S3 | 3.8 | −1.0% | −0.6% | −3.4% |
| S4 | 3.7 | 1.2% | 0.2% | 0.7% |
| R1 | 3.0 | 0.7% | 0.6% | 6.7% |
| R2 | 4.5 | 5.5% | 0.3% | 1.8% |
| R3 | 3.9 | 4.7% | 0.4% | 0.8% |

TABLE 5

Feed C: 0.5% Fructose, 0.25% LA, 1.75% HMF, 50% water, 47.5% IL

| Short Name | Liq/Solid Ratio [g/g] | Fructose Uptake [g/g solid] | LA Uptake [g/g solid] | HMF Uptake [g/g solid] |
|---|---|---|---|---|
| C2 | 2.0 | −0.2% | 0.0% | 0.0% |
| C3 | 10.0 | −0.2% | 0.9% | 15.7% |
| S1 | 9.4 | −0.7% | 0.0% | 0.5% |
| S2 | 10.3 | −1.2% | −0.1% | −0.4% |
| Z1 | 4.0 | −0.4% | −0.1% | 0.1% |
| Z2 | 4.0 | −0.3% | −0.1% | −0.3% |
| Z3 | 4.1 | −0.5% | 0.3% | 6.6% |
| C1 | 7.5 | 0.5% | 0.7% | 10.3% |
| C4 | 4.8 | −0.1% | 0.3% | 4.2% |
| S3 | 3.6 | 0.0% | 0.2% | 1.2% |
| S4 | 3.4 | 20.4% | 10.0% | 56.4% |
| R1 | 3.4 | 0.3% | 0.3% | 3.5% |
| R2 | 4.6 | −0.1% | 0.2% | 0.9% |
| R3 | 3.6 | 0.7% | −0.1% | 1.3% |

Example 2

Adsorption Separation of HMF and Imidazolium Ionic Liquid

In other embodiments adsorbent materials' selectivity for adsorbing HMF over monosaccharides such as glucose in an imidazolium based ionic liquid, are illustrated. Samples of solid adsorbent materials were contacted with a liquid mixture containing the ionic liquid [EMIM]Cl, water, and either HMF or glucose, at 60° C. under sealed air at atmospheric pressure and with constant stirring at 700 rpm for 1 hour. Each adsorbent material was tested under the same conditions with two feed liquid mixtures. Feed liquid mixture A had a nominal composition of 8.2% HMF, 13.5% water, and 78.4% [EMIM]Cl by mass. Feed liquid mixture B had a nominal composition of 0.5% glucose, 78.9% water, 20.5% [EMIM]Cl by mass. The liquid to solid mass ratio generally varied from 2 to 21 depending on the density of the adsorbent tested but the solid loose packing volume to liquid volume ratio was approximately 1.

The amount of liquid added to the solid adsorbent (or vise-versa) is preferably more than the minimum liquid volume required to fill void space between the solid adsorbent particles. The inter-particle void space is determined by the properties of a given adsorbent material (size, shape, packing density, etc.). The volume of the packed particle is the sum of the inter-particle void space and the adsorbent volume. The liquid volume is preferably greater than the volume of a packed particle bed to aid in assuring that the liquid volume is greater than the inter-particle void space. For a practical adsorption process, the liquid volume is preferably two times greater than the volume of the packed particle bed.

When the adsorption process was complete the bulk liquid phase was separated from the solid adsorbent by centrifuge-aided filtration for 60 minutes at 1500 rpm. This liquid phase and the feed liquid mixture were both analyzed using a HPLC system equipped with a BioRad HPX-97C Ca ion column and a refractive index detector. The adsorbent solid trapped on the filter was washed with known amount of water and the wash liquid was collected and analyzed on the above HPLC.

The adsorbent materials tested were C2 (activated carbon), C3 and C4 (graphitized carbon black), C15 (double-wall carbon nanotubes), R1 (macroreticular polystyrene crosslinked with divinylbenzene), R3 (cation exchange resin in H form), S1 (mesoporous silica), R2 (octadecyl-functionalized silica), S5 (cyano-functionalized silica), S6 (amino-functionalized silica), S7 (phenyl-functionalized silica), H1 (hydrotalcite), Z1 (NaY zeolite), Z2 (13X zeolite), Z3 (silicalite-1 zeolite), Z4 (faujasite zeolite), Z5 (H-mordenite zeolite), Z6 and Z7 (silicalite-1 zeolite), Z8 (HY zeolite), Z11 (CsY zeolite), and Z15 ($NH_4$ ZSM-5 zeolite).

The equilibrium concentrations in the bulk liquid phase and the solid adsorbent were calculated from the change in the liquid compositions due to adsorption. HMF adsorption capacities were estimated from data collected using the feed liquid mixture A. Glucose adsorption capacities were estimated from data collected using the feed liquid mixture B. The separation factor was calculated as the ratio of the HMF and glucose adsorption capacities. The solvent uptake, defined as the amount of ionic liquid and water held up by the adsorbent materials after centrifuge, was also calculated.

Figure 9:
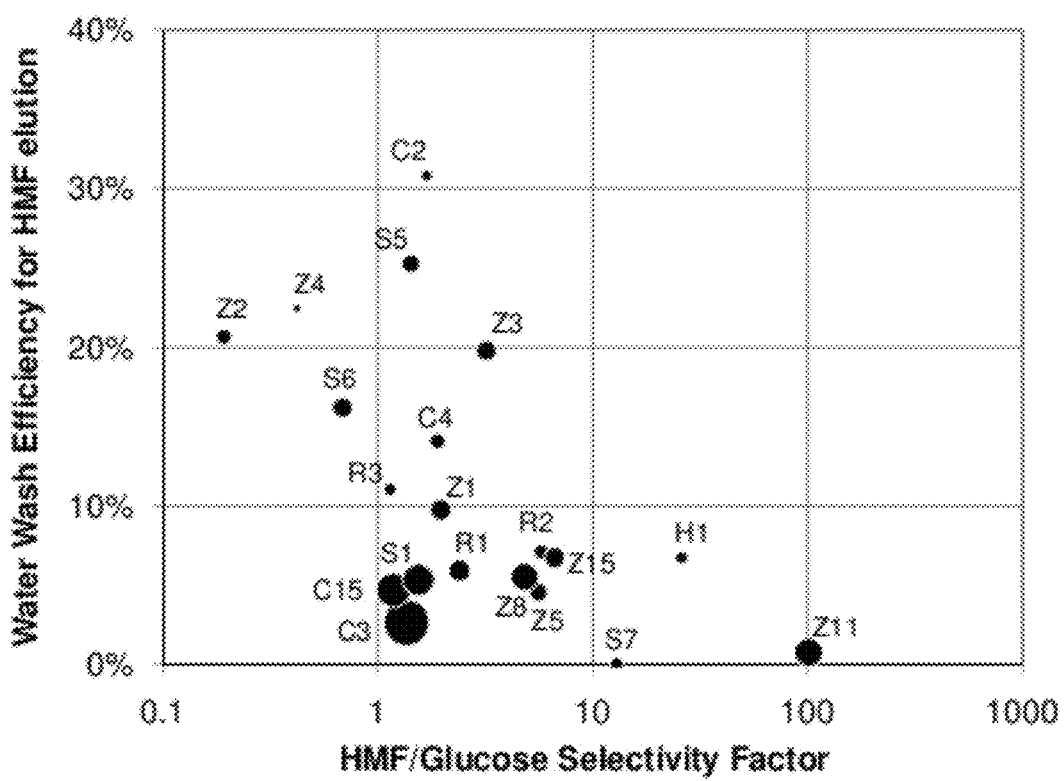
FIG. 9 is a plot diagram showing certain adsorbents' water wash efficiency for hydroxymethylfurfural (HMF) elution versus HMF/glucose separation factors determined for the adsorbents under selected conditions. The areas of the data points are proportional to the measured equilibrium capacity of HMF in the embodiments of the processes using the recited adsorbent materials.

The results of these tests are tabulated in Table 6. The amounts of HMF and glucose eluted by a water wash from the loaded adsorbent materials are set forth in Table 7. The water wash efficiency for HMF is defined as the fractional recovery of the loaded HMF normalized by the ratio of the mass of water to adsorbent. This efficiency is a measure of the ability of the adsorbents to be regenerated by water. The water wash efficiency for HMF elution is plotted against the HMF/glucose separation factor in FIG. 9, where the area of the data points are proportional to the measured equilibrium capacity of HMF in the solid adsorbents. A practical adsorbent preferably possesses a separation factor above one but also reasonable elution efficiency so that a working adsorption capacity can be maintained over multiple adsorption/regeneration cycles. About half of the adsorbents tested in this example had HMF elution efficiency above 10% and five of them above 20%. Among these five, adsorbents C2, Z3, and S5 had a greater than one separation factor. The HMF adsorption capacity of adsorbent C2 was 5.6 wt %, significantly lower than the other two. Thus, particularly suitable adsorbent materials for HMF separation for this embodiment of the disclosed processes are Z3 and S5.

Example 3

Adsorption Separation of HMF and Phosphonium Ionic Liquid

Other embodiment adsorbent materials' selectivity for adsorbing HMF over monosaccharides such as glucose in a phosphonium based ionic liquid are tested. Samples of solid adsorbent materials were contacted with a liquid mixture containing the ionic liquid Cyphos 106 (triisobutyl(methyl)phosphonium tosylate), water, and either HMF or glucose, at 60° C. under sealed air at atmospheric pressure and with

TABLE 6

| Sample ID | Equilibrium Concentrations | | | | Separation Factor HMF over glucose [—] | Solvent Uptake | | |
|---|---|---|---|---|---|---|---|---|
| | HMF | | Glucose | | | Feed A | Feed B | Average |
| | [g/g-liquid] | [g/g-solid] | [g/g-liquid] | [g/g-solid] | | [g/g-solid] | [g/g-solid] | [g/g-solid] |
| C2 | 7.6% | 5.6% | 0.5% | 0.2% | 1.7 | 0.5 | 0.6 | 0.6 |
| C3 | 6.0% | 95.2% | 0.5% | 5.6% | 1.4 | 10.1 | 10.4 | 10.3 |
| C4 | 6.6% | 11.1% | 0.5% | 0.4% | 1.9 | 0.7 | 1.0 | 0.9 |
| C15 | 6.0% | 53.5% | 0.5% | 3.5% | 1.2 | 5.6 | 6.0 | 5.8 |
| R1 | 7.5% | 21.3% | 0.6% | 0.7% | 2.4 | 1.1 | 2.5 | 1.8 |
| R2 | 6.2% | 10.5% | 0.5% | 0.2% | 5.8 | 0.5 | 0.4 | 0.5 |
| R3 | 7.8% | 7.9% | 0.6% | 0.5% | 1.1 | 0.7 | 1.7 | 1.2 |
| S1 | 7.4% | 45.7% | 0.6% | 2.3% | 1.5 | 3.6 | 5.9 | 4.7 |
| S5 | 7.5% | 15.2% | 0.5% | 0.8% | 1.4 | 1.5 | 1.8 | 1.6 |
| S6 | 5.9% | 18.9% | 0.3% | 1.4% | 0.7 | 1.6 | 2.0 | 1.8 |
| S7 | 7.2% | 9.1% | 0.5% | 0.1% | 12.9 | 0.6 | 0.4 | 0.5 |
| H1 | 5.8% | 7.5% | 0.6% | 0.0% | 26.0 | 0.2 | 0.2 | 0.2 |
| Z1 | 7.4% | 20.8% | 0.6% | 0.8% | 2.0 | 1.5 | 2.4 | 1.9 |
| Z2 | 7.0% | 11.7% | 0.2% | 1.4% | 0.2 | 1.0 | 1.3 | 1.1 |
| Z3 | 5.8% | 18.0% | 0.6% | 0.5% | 3.2 | 1.5 | 1.1 | 1.3 |
| Z4 | 6.7% | 3.5% | 0.6% | 0.7% | 0.4 | −0.4 | 1.7 | 0.6 |
| Z5 | 1.7% | 15.2% | 0.4% | 0.6% | 5.6 | 0.6 | 0.5 | 0.6 |
| Z6 | −2.4% | 25.1% | 0.6% | 1.2% | −5.3 | 9.9 | 3.0 | 6.5 |
| Z7 | −10.7% | 12.3% | 0.6% | 0.3% | −2.0 | 3.8 | 0.9 | 2.4 |
| Z8 | 7.0% | 35.3% | 0.5% | 0.6% | 4.8 | 3.1 | 1.3 | 2.2 |
| Z11 | 1.4% | 37.0% | 0.5% | 0.1% | 101.4 | 0.4 | 0.5 | 0.4 |
| Z15 | 7.4% | 18.9% | 0.6% | 0.2% | 6.6 | 1.6 | 1.2 | 1.4 |

TABLE 7

| Sample ID | Wash Ratio water/solid [g/g-solid] | HMF Recovery [—] | HMF Wash Efficiency [—] | Wash Ratio water/solid [g/g-solid] | Glucose Recovery [—] | Glucose Wash Efficiency [—] | Wash Selectivity HMF over glucose [—] | Glucose Impurity in HMF [g/g] |
|---|---|---|---|---|---|---|---|---|
| C2 | 2.3 | 71% | 31% | 2.1 | 118% | 56% | 0.6 | 7% |
| C3 | 13.7 | 36% | 3% | 13.5 | 55% | 4% | 0.7 | 8% |
| C4 | 3.2 | 44% | 14% | 3.2 | 106% | 33% | 0.4 | 9% |
| C15 | 9.1 | 43% | 5% | 9.5 | 67% | 7% | 0.7 | 9% |
| R1 | 10.3 | 61% | 6% | 10.6 | 152% | 14% | 0.4 | 7% |
| R2 | 3.4 | 24% | 7% | 3.4 | 99% | 29% | 0.2 | 6% |
| R3 | 4.2 | 46% | 11% | 4.8 | 109% | 23% | 0.5 | 14% |
| S1 | 11.5 | 62% | 5% | 11.9 | 93% | 8% | 0.7 | 7% |
| S5 | −0.1 | −3% | 25% | 3.6 | 113% | 31% | 0.8 | 210% |
| S6 | 3.6 | 58% | 16% | 0.0 | 0% | 11% | 1.5 | 0% |
| S7 | 0.0 | 0% | 0% | 2.2 | 321% | 144% | 0.0 | 100% |
| H1 | 2.4 | 16% | 7% | 2.5 | 409% | 163% | 0.0 | 9% |
| Z1 | 6.6 | 64% | 10% | 6.3 | 120% | 19% | 0.5 | 7% |
| Z2 | 3.1 | 63% | 21% | 3.2 | 65% | 20% | 1.0 | 11% |
| Z3 | 4.1 | 81% | 20% | 4.2 | 117% | 28% | 0.7 | 4% |
| Z4 | 4.2 | 93% | 22% | 4.3 | 120% | 28% | 0.8 | 21% |
| Z5 | 2.1 | 9% | 5% | 2.1 | 30% | 15% | 0.3 | 11% |
| Z6 | 4.3 | 72% | 17% | 4.5 | 68% | 15% | 1.1 | 4% |
| Z7 | 2.7 | 45% | 17% | 2.7 | 104% | 38% | 0.4 | 6% |
| Z8 | 9.9 | 55% | 6% | 9.9 | 137% | 14% | 0.4 | 4% |
| Z11 | 3.9 | 3% | 1% | 3.5 | 124% | 36% | 0.0 | 14% | constant stirring at 700 rpm for 1 hour. Each adsorbent material was tested under the same conditions with two feed liquid mixtures. Feed liquid mixture A had a nominal composition of 7.3% HMF, 12.7% water, and 80% Cyphos 106 by mass. Feed liquid mixture B had a nominal composition of 0.5% glucose, 19.4% water, and 80% Cyphos 106 by mass. The solid to liquid mass ratio generally varied from 2 to 21 depending on the density of the adsorbent tested but the solid to liquid volume ratio was approximately 1. When adsorption was complete the bulk liquid phase was separated from the solid adsorbent by centrifuge-aided filtration for 60 minutes at 1500 rpm. This liquid phase and the feed liquid mixture were both analyzed using a HPLC system equipped with a BioRad HPX-97C Ca ion column and a refractive index detector.

The adsorbent materials tested were C1 (activated carbon), C3 and C4 (graphitized carbon black), C5 to C7 (carbon molecular sieves), H1 (hydrotalcite), C15 (double-wall carbon nanotubes), R1 (macroreticular polystyrene crosslinked with divinylbenzene), R3 (cation exchange resin in H form), R4 (cation exchange resin in Ca form), S1 (mesoporous silica), S2 (porous silica), S3 and R2 (octadecyl-functionalized silica), S4 and S7 (phenyl-functionalized silica), S5 (cyano-functionalized silica), S6 (amino-functionalized silica), Z1 (NaY zeolite), Z2 (13X zeolite), and Z3 (silicalite-1 zeolite), Z4 (faujasite zeolite), and Z5 (H-mordenite zeolite).

The equilibrium concentrations in the bulk liquid phase and the solid adsorbent were calculated from the change in the liquid compositions due to adsorption. HMF adsorption capacities were estimated from data collected using the feed liquid mixture A. Glucose adsorption capacities were estimated from data collected using the feed liquid mixture B. The separation factor at the test temperature was calculated as the ratio of the HMF and glucose adsorption capacities. The solvent uptake, defined as the amount of ionic liquid and water held up by the adsorbent materials after centrifuge, was also calculated. The results are tabulated in Table 8.

Among the group of adsorbents tested, samples C7 and Z3 show greater than one separation factor for HMF over glucose. These two adsorbent materials are particularly useful adsorbents for the disclosed HMF/glucose separation processes in the ionic liquid mixtures. Adsorbent C7 is a carbon molecular sieve of pore volume 0.66 $cm^3/g$ and surface area 1500 $m^2/g$. Its porosity is distributed mainly in the mesopore range from 1.9 to 2.1 nm in diameter. Adsorbent Z3 is an organophilic zeolite of the silicalite-1 type of surface area 400 $m^2/g$. The HMF/glucose separation factors for C7 and Z3 were 3.2 and 1.5, respectively. Thus, both adsorbed HMF over glucose from the ionic liquid mixtures.

TABLE 8

| Sample ID | Equilibrium Concentrations | | | | Separation Factor HMF over glucose | Solvent Uptake | | |
|---|---|---|---|---|---|---|---|---|
| | HMF | | Glucose | | | Feed A | Feed B | Average |
| | [g/g-liquid] | [g/g-solid] | [g/g-liquid] | [g/g-solid] | [—] | [g/g-solid] | [g/g-solid] | [g/g-solid] |
| C1 | 8.7% | 8.7% | 0.3% | 2.0% | 0.2 | 1.8 | 1.7 | 1.8 |
| C3 | 7.3% | 97.4% | 0.2% | 8.6% | 0.4 | 12.3 | 11.8 | 12.1 |
| C4 | 6.5% | 7.2% | 0.3% | 1.1% | 0.3 | 0.8 | 0.8 | 0.8 |
| C5 | 6.4% | 3.9% | 0.4% | 0.5% | 0.4 | 0.3 | 0.3 | 0.3 |
| C6 | 4.5% | 19.0% | 0.3% | 1.6% | 0.7 | 1.3 | 1.3 | 1.3 |
| C7 | 2.6% | 21.8% | 0.4% | 1.0% | 3.2 | 0.9 | 0.9 | 0.9 |
| C15 | 6.9% | 46.5% | 0.3% | 5.8% | 0.3 | 6.0 | 6.0 | 6.0 |
| H1 | 7.7% | 14.2% | 0.2% | 1.5% | 0.3 | 2.0 | 2.0 | 2.0 |
| R1 | 7.3% | 18.9% | 0.3% | 2.8% | 0.3 | 2.5 | 2.5 | 2.5 |
| R2 | 7.4% | 10.3% | 0.3% | 1.4% | 0.3 | 1.4 | 1.4 | 1.4 |
| R3 | 7.9% | 7.2% | 0.4% | 1.6% | 0.2 | 1.4 | 1.5 | 1.5 |
| R4 | 7.6% | 2.6% | 0.3% | 1.4% | 0.1 | 0.5 | 0.7 | 0.6 |
| S1 | 7.4% | 45.8% | 0.2% | 4.5% | 0.3 | 6.3 | 6.5 | 6.4 |
| S2 | 7.2% | 76.8% | 0.3% | 5.8% | 0.6 | 10.3 | 6.0 | 8.2 |
| S4 | | | 0.3% | 1.6% | | | 1.7 | 1.7 |
| S5 | 7.3% | 10.4% | 0.3% | 1.7% | 0.3 | 1.4 | 1.7 | 1.6 |
| S6 | 7.1% | 8.5% | 0.3% | 1.4% | 0.3 | 1.0 | 1.2 | 1.1 |
| S7 | 3.7% | 16.1% | 0.2% | 1.3% | 0.7 | 0.7 | 0.8 | 0.7 |
| Z1 | 7.6% | 20.5% | 0.2% | 3.2% | 0.2 | 2.9 | 2.7 | 2.8 |
| Z2 | 7.8% | 18.6% | 0.1% | 2.4% | 0.1 | 2.7 | 1.8 | 2.2 |
| Z3 | 4.3% | 22.0% | 0.3% | 1.1% | 1.5 | 1.5 | 0.8 | 1.1 |
| Z4 | 6.5% | 29.9% | 0.3% | 1.5% | 0.9 | 3.8 | 1.3 | 2.5 |
| Z5 | 7.6% | 11.5% | 0.2% | 1.4% | 0.3 | 1.7 | 0.9 | 1.3 |

Example 4

Adsorption Separation of HMF and Phosphonium Ionic Liquid

Other embodiment adsorbent materials' selectivity for adsorbing HMF over monosaccharides such as glucose in a phosphonium based ionic liquid are tested. Samples from a selection of solid adsorbent materials were contacted with a liquid mixture containing the ionic liquid Cyphos 106 (tri-isobutyl(methyl)phosphonium tosylate), water, and either HMF or glucose, at 60° C. under sealed air at atmospheric pressure and with constant stirring at 700 rpm for 1 hour. Each adsorbent material was tested under identical conditions with two feed liquid mixtures. Feed liquid mixture A had a nominal composition of 7.8% HMF, 70.3% water, and 21.9% Cyphos 106 by mass. Feed liquid mixture B had a nominal composition of 0.5% glucose, 78.9% water, 20.5% Cyphos 106 by mass. The solid to liquid mass ratio generally varied from 2 to 21 depending on the density of the adsorbent tested but the solid to liquid volume ratio was approximately 1. When adsorption was complete the bulk liquid phase was separated from the solid adsorbent by centrifuge-aided filtration for 90 minutes at 1500 rpm. This liquid phase and the feed liquid mixture were both analyzed using a HPLC system equipped with a BioRad HPX-97C Ca ion column and a refractive index detector. The adsorbent solid trapped on the filter was washed with known amount of water and the wash liquid was collected and analyzed on the above HPLC.

The adsorbent materials tested were Z6 and Z7 (silicalite-1 zeolite), Z8 (HY zeolite), Z1 (NaY zeolite), Z10 (CsNaY zeolite), Z11 and Z12 (CsY zeolite), Z13 and Z14 (ZSM-5 zeolite), Z15 ($NH_4$ ZSM-5 zeolite), Z16 (silicate), C8 (multiwall carbon nanotubes), and C9 to C14 (carbon molecular sieves).

The equilibrium concentrations in the bulk liquid phase and the solid adsorbent were calculated from the change in the liquid compositions due to adsorption. HMF adsorption capacities were estimated from data collected using the feed liquid mixture A. Glucose adsorption capacities were estimated from data collected using the feed liquid mixture B. The separation factor at the test temperature was calculated as the ratio of the HMF and glucose adsorption capacities. The solvent uptake, defined as the amount of ionic liquid and water held up by the adsorbent materials after centrifuge, was also calculated. The results are tabulated in Table 9. The amounts of HMF and glucose eluted by a water wash from the loaded adsorbent materials are included in Table 10. The water wash efficiency for HMF was defined as the fractional recovery of the loaded HMF normalized by the ratio of the mass of water to adsorbent. This efficiency is a measure of the ability of the adsorbents to be regenerated by water.

Figure 10:
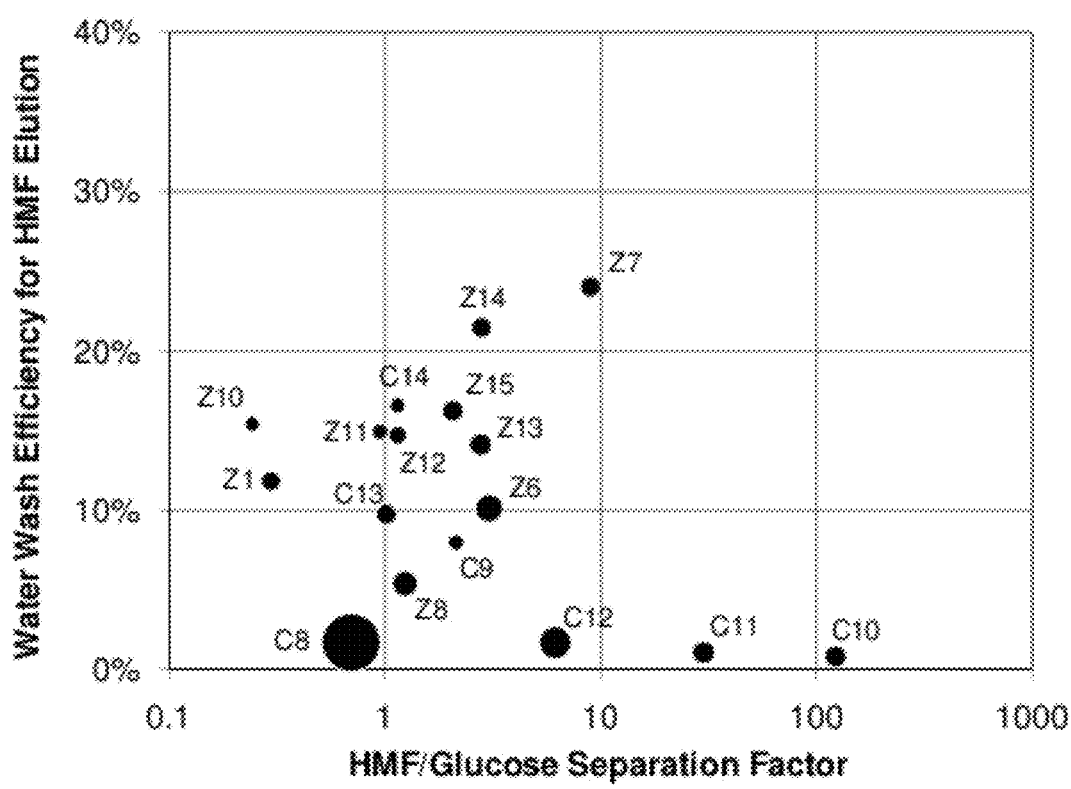
FIG. 10 is a plot diagram showing certain adsorbents' water wash efficiency for hydroxymethylfurfural (HMF) elution versus HMF/glucose separation factors determined for the adsorbents under selected conditions. The areas of the data points are proportional to the measured equilibrium capacity of HMF in the embodiments of the processes using the recited adsorbent materials.

The water wash efficiency for HMF elution was plotted against the HMF/glucose separation factor in FIG. 10, where the area of the data points are proportional to the measured equilibrium capacity of HMF in the solid adsorbents. A suitable adsorbent preferably possesses a separation factor above one and a reasonable elution efficiency (such as 5% to 95%, or 20% to 50%) so that a working adsorption capacity can be maintained over multiple adsorption/regeneration cycles.

The wash efficiency for HMF elution, or elution efficiency, is used herein to refer to a percentage of the HMF recovered in a "one-time" washing by an elution solvent, from the total amount of the adsorbed HMF divided by the mass ratio of the solvent used to the adsorbent solid. The elution efficiency will be greater than zero percent for a regenerable adsorbent material. For a given elution efficiency, high HMF recovery can be obtained by multiple washings of the column using relatively large amounts of washing solution. From a practical point of view, the elution efficiency is preferably as high as possible to save the washing solution and reduce the capital and operation costs.

Certain of the adsorbent materials have HMF elution efficiency above 10%, with Z7 and Z14 above 20%. Adsorbent materials Z6, Z7, Z13, Z14 and Z15 include both a greater than one separation factor and an elution efficiency greater than 10%. Adsorbent material Z7 has a particularly suitable elution efficiency and separation factor of 8.9. A particularly useful adsorbent material for the presently disclosed processes is Z6; although the elution efficiency of adsorbent Z6 is lower than certain adsorbents disclosed herein, it has particularly suitable HMF adsorption capacities at 27.5 wt %. Adsorbent materials Z7, Z6, and Z14 are particularly useful for practicing the presently disclosed processes. The Z6, Z7 and Z14 adsorbent materials have the same crystal phase and pore structures as the ZSM-5 and silicalite-type zeolite materials. However, these materials were prepared with smaller, more individualized crystal structures or particles. The crystal sizes are over a range of tens of nanometers to hundreds of nanometers. By contrast, the commercial zeolite materials often have crystal sizes at the level of micrometers and zeolite crystals form larger agglomerates. The smaller zeolite crystal sizes allow the HMF diffusion inside the zeolite crystal to occur faster, which benefits the adsorption process productivity.

TABLE 9

| Sample ID | Equilibrium Concentrations | | | | Separation Factor HMF over glucose | Solvent Uptake | | |
|---|---|---|---|---|---|---|---|---|
| | HMF | | glucose | | | Feed A | Feed B | Average |
| | [g/g-liquid] | [g/g-solid] | [g/g-liquid] | [g/g-solid] | [—] | [g/g-solid] | [g/g-solid] | [g/g-solid] |
| Z6 | 5.0% | 27.5% | 0.6% | 1.0% | 3.0 | 2.3 | 2.0 | 2.2 |
| Z7 | 2.8% | 15.8% | 0.5% | 0.3% | 8.9 | 0.7 | 0.5 | 0.6 |
| Z8 | 7.4% | 23.5% | 0.5% | 1.4% | 1.2 | 2.6 | 2.6 | 2.6 |
| Z1 | 7.5% | 14.0% | 0.3% | 1.9% | 0.3 | 1.7 | 2.1 | 1.9 |
| Z10 | 7.3% | 8.3% | 0.3% | 1.2% | 0.2 | 1.1 | 0.9 | 1.0 |
| Z11 | 7.3% | 10.0% | 0.5% | 0.8% | 0.9 | 1.0 | 1.4 | 1.2 |
| Z12 | 7.6% | 12.1% | 0.5% | 0.7% | 1.1 | 1.5 | 1.3 | 1.4 |
| Z13 | 5.2% | 18.4% | 0.5% | 0.6% | 2.8 | 1.1 | 1.0 | 1.1 |
| Z14 | 4.8% | 16.0% | 0.5% | 0.6% | 2.8 | 0.9 | 0.9 | 0.9 |
| Z15 | 5.2% | 16.4% | 0.5% | 0.8% | 2.1 | 1.0 | 1.0 | 1.0 |
| Z16 | 9.3% | −0.5% | 0.5% | 0.3% | −0.1 | 0.6 | 0.6 | 0.6 |
| C8 | 7.6% | 122.1% | 0.5% | 12.3% | 0.7 | 15.2 | 20.8 | 18.0 |
| C9 | 6.5% | 9.5% | 0.6% | 0.4% | 2.1 | 0.8 | 0.8 | 0.8 |
| C10 | 0.6% | 17.0% | 0.6% | 0.1% | 122.8 | 0.5 | 0.5 | 0.5 |
| C11 | 2.1% | 18.1% | 0.6% | 0.2% | 29.9 | 0.6 | 0.6 | 0.6 |
| C12 | 4.2% | 37.4% | 0.5% | 0.8% | 6.1 | 1.7 | 1.5 | 1.6 |
| C13 | 5.7% | 15.2% | 0.4% | 1.0% | 1.0 | 1.2 | 1.1 | 1.2 |
| C14 | 7.5% | 8.9% | 0.5% | 0.6% | 1.1 | 1.0 | 1.0 | 1.0 |

TABLE 10

| Sample ID | Wash Ratio water/solid [g/g-solid] | HMF Recovery [—] | HMF Wash Efficiency [—] | Wash Ratio water/solid [g/g-solid] | Glucose Recovery [—] | Glucose Wash Efficiency [—] | Wash Selectivity (HMF/glucose) HMF over glucose [—] | Glucose Impurity in HMF [g/g] |
|---|---|---|---|---|---|---|---|---|
| Z1 | 3.4 | 40% | 12% | 3.8 | 56% | 15% | 0.8 | 16% |
| Z6 | 4.0 | 40% | 10% | 3.3 | 68% | 20% | 0.5 | 6% |
| Z7 | 1.9 | 45% | 24% | 1.6 | 51% | 31% | 0.8 | 2% |
| Z8 | 6.7 | 36% | 5% | 5.3 | 44% | 8% | 0.6 | 7% |
| Z10 | 3.2 | 50% | 15% | 2.0 | 51% | 26% | 0.6 | 13% |
| Z11 | 3.6 | 54% | 15% | 3.2 | 65% | 20% | 0.7 | 9% |
| Z12 | 3.6 | 53% | 15% | 3.4 | 59% | 17% | 0.8 | 6% |
| Z13 | 3.4 | 48% | 14% | 2.5 | 33% | 13% | 1.1 | 2% |
| Z14 | 2.7 | 57% | 21% | 2.6 | 38% | 15% | 1.4 | 2% |
| Z15 | 2.8 | 45% | 16% | 2.9 | 22% | 7% | 2.2 | 2% |
| Z16 | 2.8 | −634% | −228% | 2.7 | 63% | 24% | −9.7 | 7% |
| C8 | 34.6 | 59% | 2% | 56.2 | 64% | 1% | 1.5 | 10% |
| C9 | 2.0 | 16% | 8% | 1.9 | 59% | 30% | 0.3 | 13% |
| C10 | 1.5 | 1% | 1% | 0.9 | 0% | 0% | ☐ | 0% |
| C11 | 2.0 | 2% | 1% | 1.7 | 74% | 43% | 0.0 | 25% |
| C12 | 6.1 | 10% | 2% | 5.6 | 58% | 10% | 0.2 | 11% |
| C13 | 2.6 | 25% | 10% | 2.6 | 54% | 21% | 0.5 | 13% |
| C14 | 3.2 | 53% | 17% | 2.8 | 64% | 23% | 0.7 | 7% |

Example 5

Column Adsorption Separation of HMF in Ionic Liquid Mixtures

Separation of HMF over fructose by a column packed with the adsorbent material Z6 (meso silicalite-1) was demonstrated by the longer breakthrough times for HMF than for those for fructose when an ionic liquid mixture containing both components and water, was flowed through the column. Also demonstrated is the complete or virtually complete regeneration of the adsorbent column through purging of the same with methanol or sequentially with water and methanol. The breakthrough capacity for HMF was stable over 45 adsorption/regeneration cycles. The disclosed embodiment of the present processes utilizing the disclosed sequential water and methanol regeneration method, produces a product mixture of HMF in methanol with only trace amount of fructose and ionic liquid, i.e., less than 1.0 wt %. The commercial significance of the trace compounds is relative to HMF product specifications for the desired product intended uses. In the present processes, such as impurities such as sugars, ionic liquid, and reaction intermediates in the HMF end product, are preferably less than 50 wt. % in the HMF raw product, or preferably less than 10%, or more preferably less than 1 wt %.

The adsorption column was made of stainless steel and equipped with a 0.2 μm stainless steel frit at each end. The column was 4.6 mm in inside diameter and 150 mm in length. The empty column was packed by pumping a slurry containing 2 grams of the adsorbent material and 20 ml methanol using a syringe pump filled with methanol at a constant pressure of 34.5 MPa until the flow rate became steady. A total of 1.492 grams of the adsorbent material was packed into the column by this process.

The feed liquid mixtures used in the adsorption step contained 0 to 2.8 wt % fructose, 0.49 to 9.7 wt % HMF, 49.0 to 50.2 wt % Cyphos-106, and balance water. The column temperature was maintained at 50, 70, or 90° C. and the feed liquid flow rate was maintained at 0.05 or 0.15 ml/min using a HPLC pump. Effluent samples were collected in about 2 minute intervals. The adsorption column was regenerated by purging with methanol or water and then methanol at a flow rate of 0.5 ml/min using a HPLC pump. The column temperature was maintained constant at a value from 25 to 70° C. but typically at 50° C. during regeneration. The examples herein had the adsorption column maintained isothermally, that is, the adsorbent bed temperature maintained to be uniform or substantially uniform from the inlet to the outlet. The adsorption efficiency at different temperatures was tested to assure that the adsorption process may be conducted effectively over a range of temperatures. Before switching from the feed liquid to a regeneration solvent, or from one regeneration solvent to another, the residual liquid inside the column was blown out using nitrogen gas at 6.89 MPa for 15 minutes. Regeneration effluent samples were collected in about 3 minute intervals. The liquid samples were analyzed using a HPLC system equipped with a BioRad HPX-97C Ca ion column and a refractive index detector.

Figure 11:
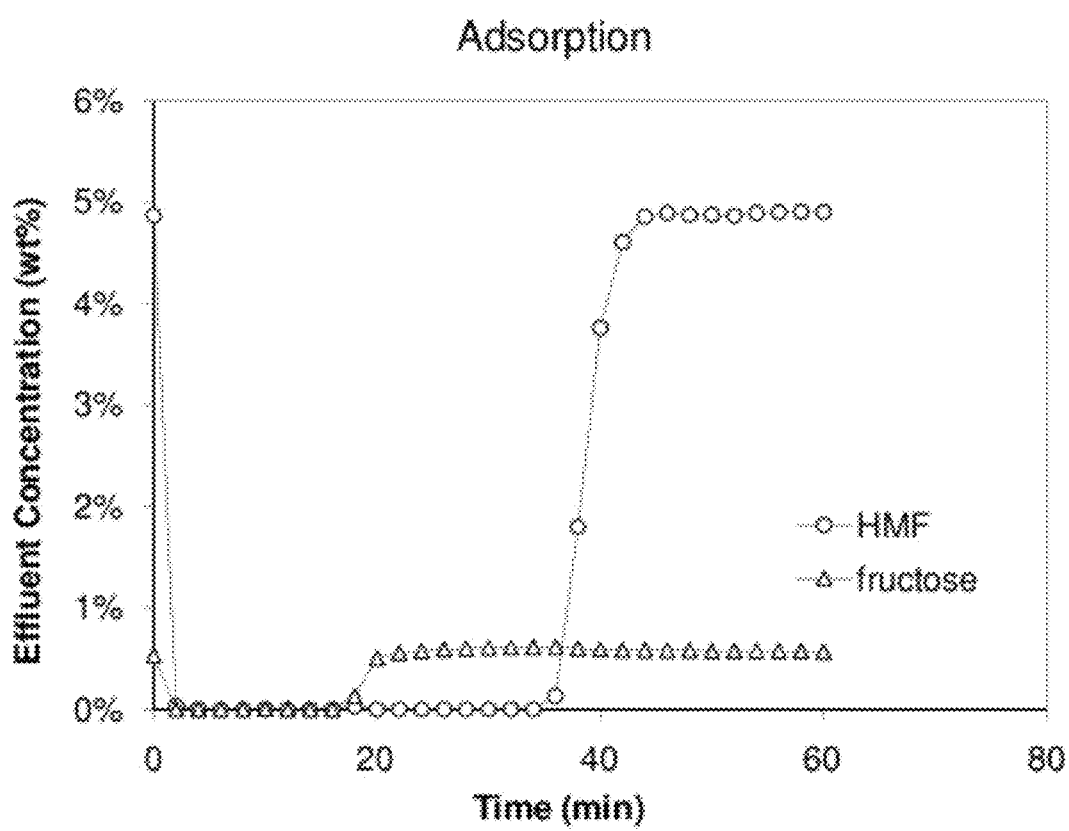
FIG. 11 is a graph showing adsorbent materials' breakthrough curves under selected conditions.
Figure 12:
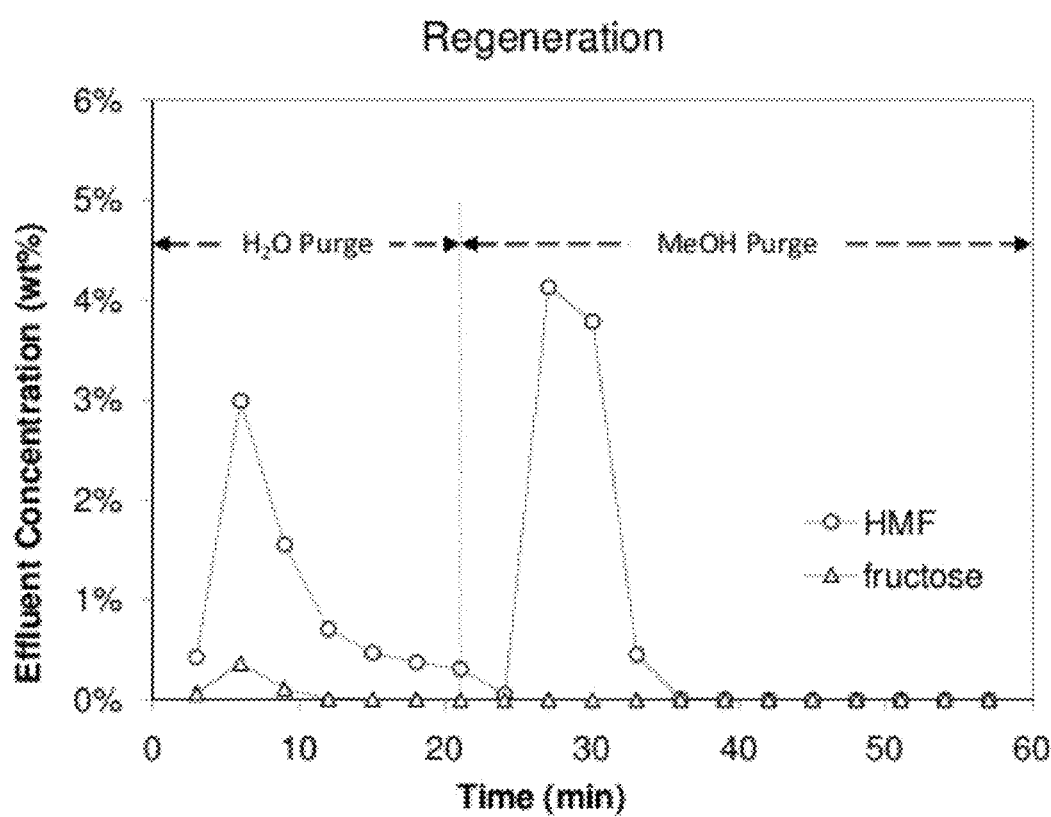
FIG. 12 is a graph showing adsorbent materials' regeneration profiles of HMF and fructose under selected conditions.

Examples of the breakthrough curves and the regeneration profiles of HMF and fructose were shown in FIGS. 11 and 12. The breakthrough curves shown in FIG. 11 were obtained using an ionic liquid mixture containing 4.9 wt % HMF and 0.54 wt % fructose at 70° C. and 0.134 ml/min. The breakthrough time for HMF in this example was approximately 36 minutes while that for fructose was about 18 minutes. The space-time for the adsorbent bed was approximately 14.5 minutes based on a bed voidage estimate of 0.782. Fructose was weakly retained by the adsorbent column compared to HMF. The adsorption capacity for HMF at complete breakthrough was approximately 0.106 gram per gram of the dry adsorbent. The adsorption capacity by the same definition for fructose was approximately 0.0006 gram per gram of the dry adsorbent.

The regeneration profiles shown in FIG. 12 were obtained by purging the column after the breakthrough experiment of FIG. 11 with water at 50° C. and 0.5 ml/min for 21 minutes followed by methanol purge at the same temperature and flow rate for 36 minutes. Both HMF and fructose were removed from the column by the water purge. However, only HMF was removed during the subsequent methanol wash. The breakdown of the amount of HMF and fructose loaded and removed during each step of the adsorption/regeneration cycle is shown in Table 11.

Figure 13:
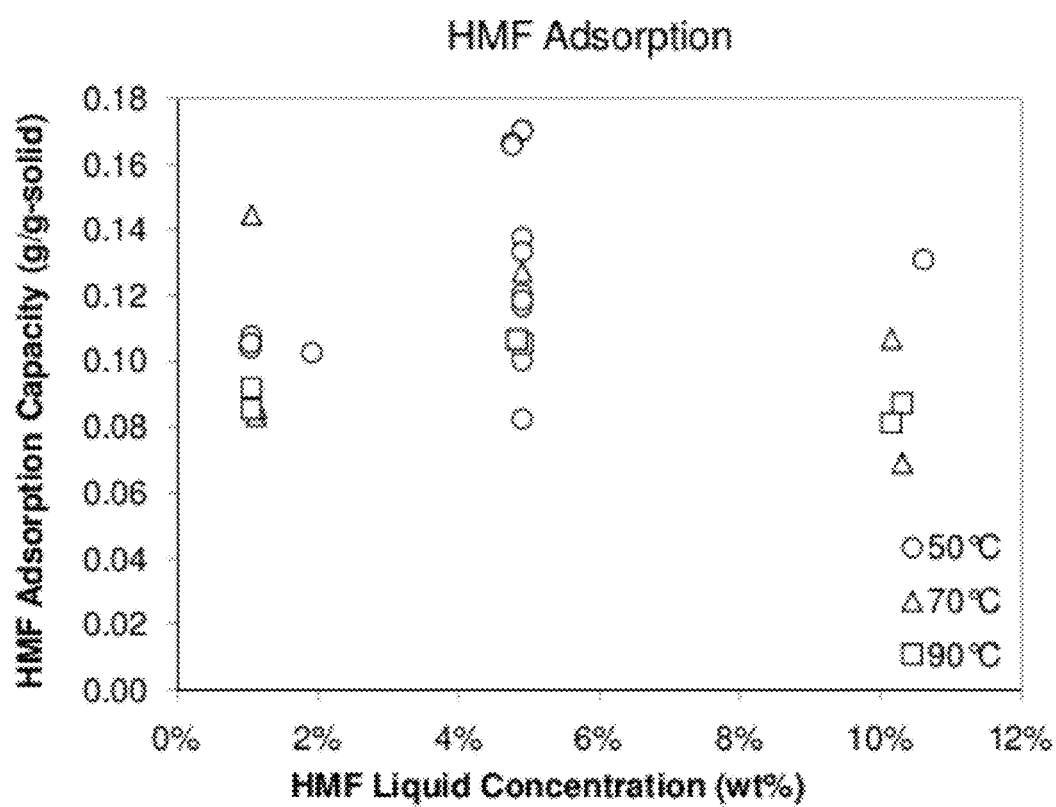
FIG. 13 is a plot diagram showing certain adsorbents' HMF adsorption capacities under selected conditions.

The adsorption capacities at complete breakthrough for HMF from the mixed solvent of Cyphos-106 and water were measured at 50, 70, and 90° C. The HMF concentration was varied from approximately 1 to 10 wt % and the fructose concentration was varied from approximately 0 to 5 wt %. The feed flow rate was varied from approximately 0.05 to 0.15 ml/min. The Z6 adsorbent column was regenerated between breakthrough tests using water and methanol purge as described above. The HMF adsorption capacity data are shown in Table 12. The same data are plotted in FIG. 13. There were weak dependencies of the HMF adsorption capacity of Z6 adsorbent on the adsorbent bed temperature and on the HMF concentration in the liquid feed mixture within the variable ranges tested. The HMF adsorption capacity is lower at higher temperature or at lower feed concentration, consistent with an equilibrium isotherm type that favors the adsorption of HMF by the solid adsorbent. The above results show that the Z6 adsorbent is particularly useful for HMF adsorption over wide temperature and concentration ranges, of from 20 to 90° C. and 0.5 to 10 wt. % HMF, which allows a relatively higher adsorption temperature to be selected to lower the viscosity of the ionic feed solution while covering the entire HMF concentration range expected for the sugar dehydration reaction products.

Figure 14:
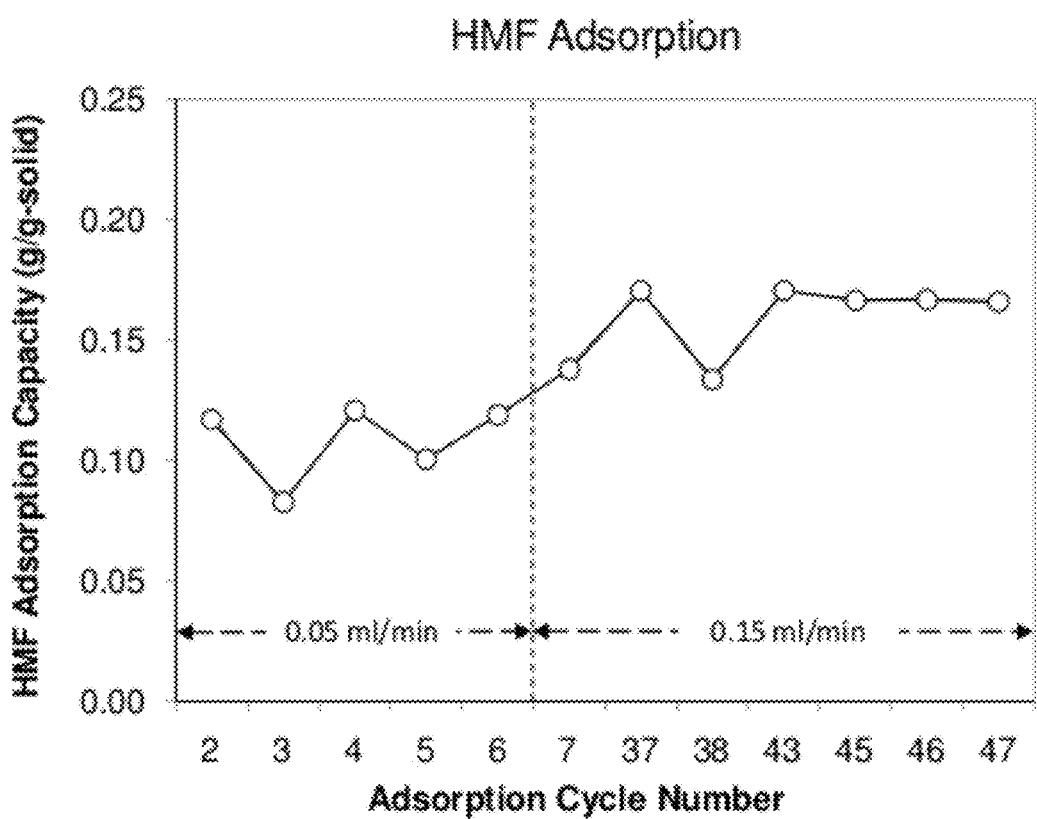
FIG. 14 is a graph showing a particular adsorbent column's adsorption HMF capacity over multiple adsorption test cycles, under selected conditions.

FIG. 14 illustrates the variation of HMF adsorption capacity of the Z6 adsorbent column over multiple test cycles of adsorption at 50° C. The data plotted are a subset of those included in Table 12. The measured HMF adsorption capacity was steady over multiple adsorption/regeneration cycles within experimental error. The average adsorption capacity at 0.15 ml/min feed flow rate was higher than at 0.05 ml/min due to the effect of mass transfer resistance.

TABLE 11

| | Adsorption | | | Regeneration | |
|---|---|---|---|---|---|
| | HMF | fructose | | HMF | fructose |
| | (g/g-dry adsorbent) | | | (g/g-dry adsorbent) | |
| Hold-up in bed void | 0.075 | 0.0087 | Purged by $N_2$ | 0.019 | 0.0029 |
| | | | Purged by $H_2O$ | 0.072 | 0.0057 |
| Adsorbed | 0.106 | 0.0006 | Purged by MeOH | 0.087 | 0.0000 |
| Total Loaded | 0.181 | 0.0093 | Total Removed | 0.178 | 0.0086 |

TABLE 12

| Test Cycle [No.] | $T_{bed, ads}$ [° C.] | $w_{0, HMF}$ [wt %] | $Q_{bed, ads}$ [ml/min] | $w_{0, fructose}$ [wt %] | $q_{0, HMF, ads}$ [g/g-solid] |
|---|---|---|---|---|---|
| 9 | 50 | 1.05% | 0.149 | | 0.108 |
| 10 | | 1.05% | 0.142 | | 0.105 |
| 11 | | 1.04% | 0.151 | | 0.104 |
| 12 | | 1.04% | 0.146 | | 0.106 |
| 1 | | 1.91% | 0.052 | 4.74% | 0.103 |
| 2 | | 4.90% | 0.050 | 0.59% | 0.117 |
| 3 | | 4.90% | 0.050 | 0.59% | 0.082 |
| 4 | | 4.90% | 0.049 | 0.59% | 0.121 |
| 5 | | 4.90% | 0.048 | 0.59% | 0.100 |
| 6 | | 4.90% | 0.049 | 0.54% | 0.119 |
| 7 | | 4.90% | 0.146 | 0.54% | 0.138 |
| 37 | | 4.90% | 0.133 | 0.54% | 0.170 |
| 38 | | 4.90% | 0.132 | 0.54% | 0.133 |
| 43 | | 4.90% | 0.151 | 0.54% | 0.170 |
| 45 | | 4.76% | 0.144 | 2.42% | 0.166 |
| 46 | | 4.76% | 0.131 | 2.42% | 0.167 |
| 47 | | 4.76% | 0.134 | 2.42% | 0.166 |
| 14 | | 10.61% | 0.151 | | 0.131 |
| 20 | 70 | 1.12% | 0.151 | | 0.083 |
| 21 | | 1.12% | 0.152 | | 0.086 |
| 22 | | 1.05% | 0.146 | | 0.145 |
| 40 | | 4.90% | 0.134 | 0.54% | 0.106 |
| 41 | | 4.90% | 0.133 | 0.54% | 0.127 |
| 15 | | 10.31% | 0.140 | | 0.069 |
| 17 | | 10.16% | 0.136 | | 0.107 |
| 23 | 90 | 1.05% | 0.153 | | 0.085 |
| 24 | | 1.05% | 0.150 | | 0.092 |
| 42 | | 4.90% | 0.133 | 0.54% | 0.105 |
| 44 | | 4.83% | 0.133 | 0.98% | 0.107 |

TABLE 12-continued

| Test Cycle [No.] | $T_{bed, ads}$ [° C.] | $w_{0, HMF}$ [wt %] | $Q_{bed, ads}$ [ml/min] | $w_{0, fructose}$ [wt %] | $q_{0, HMF, ads}$ [g/g-solid] |
|---|---|---|---|---|---|
| 16 | | 10.31% | 0.145 | | 0.087 |
| 18 | | 10.16% | 0.145 | | 0.081 |

$T_{bed, ads}$ - adsorbent bed temperature during adsorption;
$w_{0, HMF}$ - mass fraction of HMF in a liquid mixture;
$w_{0, fructose}$ - mass fraction of fructose in a liquid mixture;
$q_{0, HMF, ads}$ - HMF adsorption capacity per gram of a dry adsorbent;
$Q_{bed, ads}$ - liquid feed flow rate during a column adsorption testing Example 6

Column Adsorption Separation of Fructose Dehydration Product Mixtures Containing HMF The separation performance of a Z6 adsorbent column was demonstrated using product mixtures from the dehydration reaction of fructose in an ionic liquid. HMF was well separated from other components in the feed liquid mixture such as fructose and certain unidentified reaction byproducts that were most likely only partially dehydrated and/or dehydrogenated sugars. The adsorption capacity of HMF was not affected by the presence of the reaction byproducts. The loaded column was regenerated by the same method described in Example 5. Unreacted fructose, reaction byproducts, and hold-up ionic liquid can be recovered by water purge as an aqueous solution, which can be recycled back to dehydration reaction after water removal. HMF can be recovered by a methanol purge free of the above components.

The adsorbent column used in this experiment was the same as described in Example 5. The feed mixture was prepared by diluting with water the product mixture of a 10 minute batch reaction of 25 wt % fructose in Cyphos-106 at 110° C. The composition of the feed mixture was HMF 4.66 wt %, fructose 2.31 wt %, byproducts 6.18 wt %, Cyphos-106 49.91 wt %, and balance water. The adsorption step was carried out at 50° C. with a feed flow rate of 0.132 ml/min. The regeneration step was carried out at 50° C. with a solvent purge flow rate of 0.5 ml/min. Other experimental conditions were the same as set forth in Example 5.

The breakthrough curves and the regeneration profiles of HMF, fructose, and the reaction byproduct are shown in FIGS. 15 and 16. The breakthrough time for HMF was approximately 38 minutes while that for fructose or byproducts was about 18 minutes. The space-time for the adsorbent bed was approximately 14.7 minutes based on a bed voidage estimate of 0.782. HMF was clearly well separated from fructose and the byproducts with the latter two only weakly retained by the adsorbent column. The adsorption capacity for HMF at complete breakthrough was approximately 0.116 gram per gram of the dry adsorbent. The adsorption capacities for fructose and the byproducts were negligible (i.e., less than 1 wt. %), compared to measurement error.

FIG. 15 illustrates breakthrough curves of HMF and fructose on a Z6 adsorbent column (test run at 50° C., 0.132 ml/min, feed liquid composition 4.66 wt % HMF, 2.31 wt % fructose, 6.18 wt % byproduct, 49.91 wt % Cyphos-106, and balance water) and the ionic liquid pressure profile. FIG. 16 illustrates regeneration profiles of HMF, fructose, and byproduct on a Z6 adsorbent column (test run at 50° C., 0.5 ml/min, purge solvent switch from water to methanol at 18 minute) and the ionic liquid pressure profile during adsorption. The regeneration profiles shown in FIG. 16 were obtained by purging the column after the breakthrough experiment of FIG. 15 with water at 50° C. and 0.5 ml/min for 18 minutes followed by methanol purge at the same temperature and flow rate for 42 minutes. Fructose and the byproducts were removed from the column by the water purge. A portion of HMF was also removed by the water purge, for example, as shown in Table 13. The portion of HMF removed by water purge (0.08 g/g-sorbent) was slightly over the amount hold-up in bed void space, i.e., non-adsorbed (0.072 g/g-sorbent). Out of the adsorbed HMF (0.117 g/g-sorbent) about 80% was recovered by methanol regeneration (0.093 g/g-sorbent). Thus, the water purge had only a small effect on HMF recovery in a one-pass process. The HMF removed by the water purge is recycled to the adsorption process so the effect on the overall recovery is even smaller. Only HMF was removed during the subsequent methanol wash. The breakdown of the amount of HMF and fructose loaded and removed during each step of the adsorption/regeneration cycle is shown in Table 13.

TABLE 13

| | Adsorption | | | | Regeneration | | |
|---|---|---|---|---|---|---|---|
| | HMF | Fructose | byproduct | | HMF | fructose | byproduct |
| | (g/g-dry adsorbent) | | | | (g/g-dry adsorbent) | | |
| Hold-up in bed void | 0.072 | 0.036 | 0.096 | Purged by $N_2$ | 0.017 | 0.009 | 0.024 |
| | | | | Purged by $H_2O$ | 0.080 | 0.025 | 0.062 |
| Adsorbed | 0.117 | −0.001 | −0.001 | Purged by MeOH | 0.093 | 0.000 | 0.001 |
| Total Loaded | 0.188 | 0.035 | 0.095 | Total Removed | 0.190 | 0.035 | 0.086 |

Example 7

Isolation of HMF from a Fructose Dehydration Product Mixture Using an Adsorbent Column In another embodiment of the disclosed separation process, HMF was isolated from a fructose dehydration product mixture in an ionic liquid by adsorption using a column packed with the Z6 adsorbent. HMF in the feed mixture was separated from fructose and other components by selectively loading of HMF by the adsorbent. The bulk feed liquid was removed from the column after adliquid was in the form of a mixture with water in the water wash product and a mixture with methanol in the portion of sorption by a $N_2$ purge followed by a water purge. A fructose-free solution of HMF in methanol was recovered in subsequent methanol purge. A final product of 85.2 wt % HMF was obtained by removing methanol by evaporation. The recovery of HMF from the feed mixture to the final product was 37.8%. Taking into account the loss of ionic liquid as impurity in the final product, the recovery of ionic liquid was 99.4%. The recovered ionic methanol wash product not used for isolating the final HMF product.

The adsorbent column used was the same as in Example 5. The feed mixture was prepared by diluting with water the product mixture of a 10 minute batch reaction of 25 wt % fructose in Cyphos-106 at 110° C. The composition of the feed mixture was HMF 4.80 wt %, fructose 2.57 wt %, 46.20 wt % Cyphose-106, trace glucose, formic acid, and levulinic acid, and balance water. The column was loaded at 0.15 ml/min feed flow rate and at 50° C. for 35 minutes. The liquid hold-up in the column was blown out by a $N_2$ purge at 1000 psig for 15 minutes. The column was then purged with water at 0.5 ml/min and 50° C. for 48 minutes. The column liquid hold-up was again removed by $N_2$ purge at 1000 psig for 15 minutes. The column was then purged with methanol at 0.5 ml/min and 50° C. Column effluent from 0 to 11 minutes during the methanol purge was collected and loaded in a rotary evaporator to remove methanol at room temperature under a vacuum of 11 torr for 2 hours. The final product was analyzed for composition by the same HPLC analysis method used in the previous Examples.

TABLE 14

| Stream | Mass [g] | HMF | Cyphos-106 | glucose | fructose | formic acid | levulinic acid | byproducts |
|---|---|---|---|---|---|---|---|---|
| | | | | [g/g] | | | | |
| Feed Mixture | 5.353 | 4.8% | 46.2% | 0.4% | 2.6% | 0.1% | 0.0% | 0.0% |
| MeOH Purge Product | 3.4896 | 2.7% | 0.2% | 0.0% | 0.0% | 0.0% | 0.0% | 0.0% |
| Isolated Product | 0.114 | 85.2% | 12.2% | 0.0% | 0.7% | 0.0% | 1.3% | 0.6% |
| Recovery | | 37.8% | 99.4% | | | | | |

As used herein, "comprising" means "including" and the singular forms "a" or "an" or "the" include plural references unless the context clearly dictates otherwise. The term "or" refers to a single element of stated alternative elements or a combination of two or more elements, unless the context clearly indicates otherwise.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting. Other features of the disclosure are apparent from the following detailed description and the claims.

Unless otherwise indicated, all numbers expressing quantities of components, molecular weights, percentages, temperatures, times, and so forth, as used in the specification or claims are to be understood as being modified by the term "about." Accordingly, unless otherwise indicated, implicitly or explicitly, the numerical parameters set forth are approximations that may depend on the desired properties sought and/or limits of detection under standard test conditions/methods. When directly and explicitly distinguishing embodiments from discussed prior art, the embodiment numbers are not approximates unless the word "about" is recited.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A separation process comprising:
    (a) providing an ionic liquid catalysis reaction mixture including an ionic liquid, an unreacted sugar compound, and a predetermined reaction product of an ionic liquid catalysis reaction;
    (b) flowing the ionic liquid catalysis reaction mixture into a first vessel having a solid porous adsorption material having an adsorption affinity for the predetermined reaction product;
    (c) collecting separated ionic liquid and unreacted sugar compound eluting from the first vessel;
    (d) desorbing the predetermined reaction product from the solid porous adsorption material in the first vessel with a fluid flow stream; and
    (e) collecting the desorbed predetermined reaction product eluted with the fluid flow stream.

2. The separation process of claim 1 wherein the predetermined reaction product of an ionic liquid catalysis reaction is HMF, C5-C6 molecules of an aromatic ring compound of dehydrated sugar molecules and/or de-oxygenated sugar molecules an HMF derivative, or mixtures thereof.

3. The separation process of claim 1 wherein the predetermined reaction product of an ionic liquid catalysis reaction is HMF.

4. The separation process of claim 1 wherein the ionic liquid acts as both a solvent and a catalyst in an ionic liquid catalysis reaction.

5. The separation process of claim 1 wherein the ionic liquid is triisobutyl(methyl)phosphonium tosylate and/or 1-ethyl-3-methylimidazolium chloride.

6. The separation process of claim 2 wherein the ionic liquid is triisobutyl(methyl)phosphonium tosylate and/or 1-ethyl-3-methylimidazolium chloride.

7. The separation process of claim 1 wherein the solid porous adsorption material comprises zeolite.

8. The separation process of claim 1 wherein the solid porous adsorption material comprises one or more of carboxen 1012, organophilic zeolite, molecular sieve, pinnacle II phenyl bulk packing, carboxen 1003, porous silica, carboxen 1021, carbon black, carbopack X, MCM-41, PLC-18, DWNTS, synthetic hydrotalcite, amberlite XAD-1180, pinnacle II amino bulk packing, pinnacle II cyano bulk packing, BCR-704, amberlyst 16 wet, activated charcoal, dowex monosphere 99ca/320,1, phenyl-functionalized silica gel.

9. The separation process of claim 1 wherein the solid porous adsorption material comprises one or more of activated carbon, graphitized carbon black, or carbon molecular sieve, the solid porous adsorption material having a mean pore size of 1 nm to 5 nm.

10. The separation process of claim 1 wherein the solid porous adsorption material comprises carbon black, the solid porous adsorption material having a surface area of 500 $m^2/g$ or greater and a mean pore size of 1 nm to 5 nm.

11. The separation process of claim 1 wherein the solid porous adsorption material comprises zeolite of MFI-type lattice structures of Si/Al ratio of at least 10 having a silicon to aluminum ratio of greater than 10 and having a MFI-type lattice structure ion exchanged with alkaline, alkaline earth metal ions or mixtures thereof.

12. The separation process of claim 1 wherein the solid porous adsorption material is zsm-5 zeolite, silicalite zeolite, silicalite-1 zeolite of crystal sizes from 10 nm to 300 nms.

13. The separation process of claim 1 wherein the solid porous adsorption material is zeolite faujasite having a silicon to aluminum ratio of from 2 to 100.

14. The separation process of claim 1 wherein the solid porous adsorption material comprises silicalite zeolite, and/or silicalite-1, that are substantially free of aluminum.

15. The separation process of claim 1 wherein the unreacted sugar compound is fructose or glucose.

16. The separation process of claim 1 further comprising mixing the ionic liquid catalysis reaction mixture with de-ionized water to make a water solution mixture, and flowing the water solution mixture into the first vessel.

17. The separation process of claim 1 wherein the ionic liquid catalysis reaction mixture comprises 0.1% to 99% ionic liquid, 0% to 95% water, 0.1% to 29% unreacted sugar compound, and 1 to 50% of the predetermined reaction product.

18. The separation process of claim 17 wherein the predetermined reaction product is HMF.

19. The separation process of claim 1 wherein the ionic liquid catalysis reaction mixture is flowed in the first vessel having a solid porous adsorption material comprising adsorbent particles with a mean particle size of 0.1 mm to 10 mm, at a liquid-hourly space velocity of 0.1 to 100 1/h through the first vessel.

20. The separation process of claim 1 wherein the solid porous adsorption material is structured in the first vessel to form an array of parallel flow channels and flowing the ionic liquid catalysis reaction mixture through the parallel flow channels of the first vessel at a liquid-hourly space velocity of 0.1 to 100 1/h.

21. The separation process of claim 19 wherein the solid porous adsorption material comprises adsorbent particles with a mean pore size of 0.1 mm to 3 mm.

22. The separation process of claim 1 wherein the fluid flow stream comprises water, methanol, ethanol, liquid-phase $CO_2$ or mixtures thereof.

23. The separation process of claim 1 wherein the fluid flow stream comprises alcohol.

24. The separation process of claim 1 wherein desorbing the predetermined reaction product from the solid porous adsorption material in the first vessel first comprises flowing an inert gas through the first vessel, purging residual solution from the first vessel, and then desorbing the predetermined reaction product from the solid porous adsorption material with a second fluid flow stream in the first vessel.

25. A separation process comprising:
    (a) providing an ionic liquid catalysis reaction mixture including HMF, triisobutyl(methyl)phosphonium tosylate, and an unreacted sugar compound;
    (b) mixing the ionic liquid catalysis reaction mixture with de-ionized water to make a water solution mixture;
    (c) flowing the water solution mixture into an adsorption material column packed with particles of one or more of zeolite zsm-5, zeolite silicalite-1, activated carbon, graphitized carbon black, carbon molecular sieve, or mixtures thereof, the column at a temperature from 20 to 200° C.;

(d) collecting separated triisobutyl(methyl)phosphonium tosylate and the unreacted sugar compound fractions of the ionic liquid catalysis reaction mixture at different elution times;

(e) desorbing HMF from adsorption material in the column with a water-based fluid at a temperature from 20 to 200° C.;

(f) collecting desorbed HMF; and (g) directly reusing the eluted triisobutyl(methyl)phosphonium tosylate for another ionic liquid catalysis reaction.

26. A separation process comprising:

(a) providing an ionic liquid catalysis reaction mixture including HMF, 1-ethyl-3-methylimidazolium chloride, and an unreacted sugar compound;

(b) mixing the ionic liquid catalysis reaction mixture with de-ionized water to make a water solution mixture;

(c) flowing the water solution mixture into an adsorption material column packed with particles of one or more of cyano functionalized silica, zeolite silicalite-1 organophilic molecular sieve, activated carbon, graphitized carbon black, macroreticular polystyrene DVB, or mixtures thereof, the column at a temperature from 20 to 200° C.;

(d) collecting separated 1-ethyl-3-methylimidazolium chloride and the unreacted sugar compound fractions of the ionic liquid catalysis reaction mixture at different elution times;

(e) desorbing HFM from adsorption material in the column with a water-based fluid at a temperature from 20 to 200° C.; and (f) collecting desorbed HMF; and (g) directly reusing the eluted 1-ethyl-3-methylimidazolium chloride for another ionic liquid catalysis reaction.

* * * * *

UNITED STATES PATENT AND TRADEMARK OFFICE
CERTIFICATE OF CORRECTION

PATENT NO. : 8,236,973 B2
APPLICATION NO. : 12/756916
DATED : August 7, 2012
INVENTOR(S) : Wei Liu et al.

Page 1 of 1

It is certified that error appears in the above-identified patent and that said Letters Patent is hereby corrected as shown below:

In the Specification:

In column 35, lines 52-57, the words "The bulk feed liquid was removed from the column after adliquid was in the form of a mixture with water in the water wash product and a mixture with methanol in the portion of sorption by a $N_2$ purge followed by a water purge." should read -- The bulk feed liquid was removed from the column after adsorption by a $N_2$ purge followed by a water purge. --.

In column 35, lines 64-66, the words "The recovered ionic methanol wash product not used for isolating the final HMF product." should read -- The recovered ionic liquid was in the form of a mixture with water in the water wash product and a mixture with methanol in the portion of methanol wash product not used for isolating the final HMF product. --.

In the Claims:

In column 37, line 39, the words "molecules an" should read -- molecules, an --.

Signed and Sealed this
Fifth Day of March, 2013

Teresa Stanek Rea
*Acting Director of the United States Patent and Trademark Office*